US012285018B2

(12) United States Patent
Goormachtig et al.

(10) Patent No.: US 12,285,018 B2
(45) Date of Patent: Apr. 29, 2025

(54) PLANT GROWTH PROMOTING MICROBIAL COMPOSITIONS

(71) Applicants: VIB VZW, Ghent (BE); UNIVERSITEIT GENT, Ghent (BE); INSTITUUT VOOR LANDBOUW-EN VISSERIJONDERZOEK (ILVO), Merelbeke (BE)

(72) Inventors: Sofie Goormachtig, Ghent (BE); Stien Beirinckx, Ghent (BE); Jane Debode, Merelbeke (BE)

(73) Assignees: Universiteit Gent, Ghent (BE); VIB VZW, Ghent (BE); ILVO, Merelbeke (BE)

( * ) Notice: Subject to any disclaimer, the term of this patent is extended or adjusted under 35 U.S.C. 154(b) by 902 days.

(21) Appl. No.: 17/434,180

(22) PCT Filed: Feb. 25, 2020

(86) PCT No.: PCT/EP2020/054909

§ 371 (c)(1),
(2) Date: Aug. 26, 2021

(87) PCT Pub. No.: WO2020/173941

PCT Pub. Date: Sep. 3, 2020

(65) Prior Publication Data

US 2022/0167625 A1 Jun. 2, 2022

(30) Foreign Application Priority Data

Feb. 27, 2019 (GB) ..................................... 1902612

(51) Int. Cl.

| | |
|---|---|
| ***A01N 63/20*** | (2020.01) |
| ***C12N 1/20*** | (2006.01) |
| *C12R 1/01* | (2006.01) |

(52) U.S. Cl.

CPC ............. *A01N 63/20* (2020.01); *C12N 1/205* (2021.05); *C12R 2001/01* (2021.05)

(58) Field of Classification Search

CPC .......... A01N 63/20; C12N 1/20; C12N 1/205; C12R 2001/01

See application file for complete search history.

(56) References Cited

FOREIGN PATENT DOCUMENTS

WO 2016130586 A2 8/2016

OTHER PUBLICATIONS

Bhattachary YA, P.N. et al. "Plant growth-promoting rhizobacteria (PGPR): emergence in agriculture." Worl Journal of Microbiology and Biotechnology, Kluwer Academic Publishers, Dec. 24, 2011, vol. 28, No. 4 pp. 1327-1350.

PCT International Search Report and Written Opinion; Application No. PCT/EP2020/054909 VIB VZW, International filing date of Feb. 25, 2020, date of mailing Jul. 20, 2020, 15 pages.

Yang, Endong, et al., "Complete genome sequence of Caulobacter flavus RHGG3T, a type species of the genus Caulobacter with plant growth-promoting traits and heavy metal resistance" 3 Biotech, (2019) vol. 9, No. 2, 8 pgs.

*Primary Examiner* — Bao Q Li

(74) *Attorney, Agent, or Firm* — Patent Law Works LLP

(57) ABSTRACT

The present invention relates to the field of sustainable agriculture. Specifically, the invention provides microbial compositions and methods useful for the production of crop plants. In particular, the compositions and methods disclosed herein are useful for enhancing plant growth and/or plant yield as well as for promoting cold and salt tolerance.

9 Claims, 7 Drawing Sheets

Specification includes a Sequence Listing.

PLANT GROWTH PROMOTING MICROBIAL COMPOSITIONS

CROSS-REFERENCE TO RELATED APPLICATIONS

This application is a national phase entry under 35 U.S.C. § 371 of International Patent Application PCT/EP2020/054909, filed Feb. 25, 2020, designating the United States of America and published in English as International Patent Publication WO 2020/173941 on Sep. 3, 2020, which claims the benefit under Article 8 of the Patent Cooperation Treaty to Great Britain Patent Application Serial No. 1902612.9, filed Feb. 27 2019, the entireties of which are hereby incorporated by reference.

FIELD OF THE INVENTION

The present invention relates to the field of sustainable agriculture. Specifically, the invention provides microbial compositions and methods useful for the production of crop plants. In particular, the compositions and methods disclosed herein are useful for enhancing plant growth and/or plant yield as well as for promoting cold and salt tolerance.

BACKGROUND

Agriculture in developed countries has become increasingly dependent on chemical fertilizers and pesticides in order to achieve and/or maintain high crop yields. Given the negative environmental impact of some of these agricultural aids, there is a growing interest to improve crop yield using eco-friendly and more sustainable approaches. A promising practice is the use of microorganisms that enhance plant growth, increase tolerance to unfavorable soil and/or environmental conditions, and/or improve the plant's resource use efficiency. Those micro-organisms that live closely associated with the root system of crops in a mutualistic way are often referred to as plant-growth-promoting rhizobacteria (PGPR).

The diversity of microorganisms in the soil is huge and a few grams of soil contain already hundred millions to billions microorganisms (Kumar 2016, In: K. R. Hakeem et al. (eds.), Plant, Soil and Microbes). Moreover, any microbial agent added to the rhizosphere has to interact not only with the plant in a positive way but has also to interact with any other organism sharing the same ecological niche. To be successful the inoculant has to maintain a critical population mass in the soil, out-compete other microbes for resources and have the right conditions to exert its beneficial activity (Pereg and McMillan 2015, Soil Biology and Biochemistry 80: 349-358). Hence, identifying microorganisms that support the plant's growth and vigour is a very challenging and non-obvious endeavour. Several bacteria have already been disclosed that increase plant growth and/or reduce susceptibility to diseases caused by fungi, bacteria, viruses or other plant pathogens (e.g. lose as et al 2005, Appl Environ Microbiol 71: 4951-4959; Singh et al 2011, Agric Ecosyst Environ 140: 339-353; WO2014/201044; W02013/090628; EP0256889). Other PGPR act as elicitors of tolerance to abiotic stresses, such as drought, salt and nutrient deficiency (Yang et al 2009 Trends Plant Sc 14: 1-4). Yet, the need to identify new microorganisms that promote growth of crop plants persists.

SUMMARY

Through a microbial screen for plant-growth-promoting endophytic bacteria in maize a *Caulobacter* strain, a *Bosea* strain and a *Pseudoduganella* strain were identified. Based on 16S rRNA sequence analyses said strains are all novel. In current application it is disclosed that inoculation of plant seeds or seedlings with the herein described *Caulobacter, Bosea* or *Pseudoduganella* strains improve said plant's tolerance toward cold temperatures. For the herein described *Caulobacter* strain an improved tolerance towards salt stress could be demonstrated as well.

It is an object of current application to improve growth, yield, cold tolerance and/or salt tolerance of plants. For that purpose, current application provides an isolated bacterial strain comprising a 16S rRNA sequence exhibiting at least 99.6% sequence identity to SEQ ID No. 1 or at least 99.2% sequence identity to SEQ ID No. 2 or at least 99.4% sequence identity to SEQ ID No. 3. Agricultural compositions comprising at least one of said bacterial strains are provided as well as plant seeds coated with at least one of said bacterial strains. Given that the bacterial strains disclosed in current application are especially useful in the field of agriculture, methods are provided for enhancing growth, yield, cold tolerance and/or salt tolerance of plants by administration of said bacterial strains to said plants. It is envisaged that said bacteria can be administered by several ways, for example but not limited to by coating plant seeds, inoculating the soil or other plant growth supporting media, spraying or irrigating plants.

DEPOSIT OF BIOLOGICAL MATERIAL

Purified cultures of the microbial strains described in present application were deposited at the BCCM (Belgian Coordinated Collections of Microorganisms) consortium (BCCM represented by Laboratorium voor Microbiologie-Bacterienverzameling (LMG), Universiteit Gent, K. L. Ledeganckstraat 35, 9000 Gent, Belgium), recognized as an International Depositary Authority by the World Intellectual Property organization since Mar. 1, 1992 and in accordance with the Budapest Treaty as specified in Rule 31(1) EPC2000 for the purpose of patent procedure and the regulations thereunder. The *Caulobacter* strain of current application has been deposited as *Caulobacter* sp. RHG1 with deposit number LMG P-31259. The *Bosea* strain of current application has been deposited as lose asp. RHGS with deposit number LMG P-31260. The *Pseudoduganella* strain of current application has been deposited as *Pseudoduganella* sp. RHG12 with deposit number LMG P-31261. Original deposits have been done on Feb. 7, 2019.

DESCRIPTION OF THE DRAWINGS

FIG. 1A shows the total fresh weight in mg as well as the fresh weight of shoot and root of RHG1-treated plants compared to that of mock-treated plants at 18 days after initiation of germination (DAIG). FIG. 1B shows the size of the third leaf in $mm^2$ of RHG1-treated versus mock-treated Arabidopsis plants at 18 DAIG. FIG. 1C shows the number of leaves of RHG1-treated versus mock-treated Arabidopsis plants at 18 DAIG. FIG. 1**D shows the average number of pavement cells, guard cells, and total cells per leaf of RHG1-treated versus mock-treated Arabidopsis plants at 18 DAIG. *, $p<0.05$.

FIG. 2A shows the lateral root number of RHG1-treated versus mock-treated Arabidopsis plants at 14 DAIG. FIG. 2B shows the lateral root density of RHG1-treated versus mock-treated Arabidopsis plants at 14 DAIG.

FIG. 4A, leaf surface; FIG. 4B, root tip; FIG. 4C, lateral root emergence.

FIG. 7A shows the shoot fresh weight (at 30 days after germination) in g of mock-treated and *Caulobacter*-inoculated lettuce plants in a hydroponic set-up. *, p<0.05. FIG. 7B shows the root fresh weight (at 30 days after germination) in g of mock-treated and *Caulobacter*-inoculated lettuce plants in a hydroponic set-up. *, p<0.05. FIG. 7C shows the shoot fresh weight (at six weeks after sowing) in g of mock-treated and *Caulobacter*-inoculated lettuce plants grown in peat blocks. **, p<0.01.

FIG. 8A shows the total, root and shoot fresh weight of tomato plants grown at 150mM NaCl. Plants were mock-treated or RHG1-treated and weights were determined after 18 days of growth in salt conditions. ***, p<0.001. FIG. 8B shows the average rosette size in $cm^2$ of mock-treated or RHG1-treated plants grown at 150mM NaCl.*, p<0.05.

DETAILED DESCRIPTION

Figure 1A:
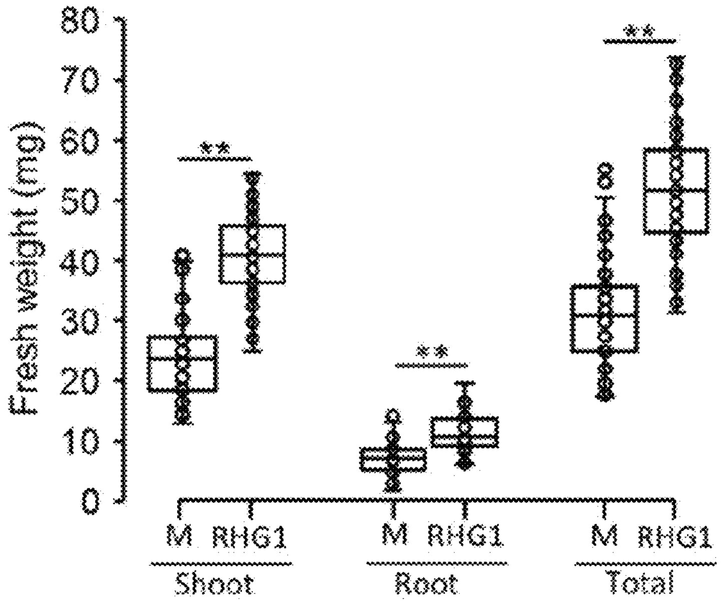
FIGS. 1A-1D shows the plant growth promoting effect of *Caulobacter* strain RHG1. Arabidopsis seeds were mock-treated or inoculated with RHG1 and grown in an in vitro system. M, mock. The plot graphs are based on three biological replicates (n≥12 for each treatment). Asterisks indicate statistical significance between mock and inoculated plants (, $p<0.01$, Student's t-test).

Diverse plant-associated microorganisms can positively impact plant health and physiology in a variety of ways and are generally referred to as plant growth promoting (PGP) microorganisms. The term "plant growth promoting" as used herein, refers to a promoting effect on a wide range of growth and development properties of cultured plants or crops, including but not limited to increased root development, increased leaf area, increased plant yield, increased fresh or dry weight, increased seed germination, increased photosynthesis, increase in accumulated biomass of the plant, increased nitrogen fixation or increased efficiency of nutrients such as nitrogen, phosphorus or potassium. Cold temperature is one of the major abiotic stress factors for juvenile maize growth due to its subtropical origin resulting in decreased yield (Leipner & Stamp 2009 In: Bennetzen J L, Hake S (eds) Springer, New York, pp 291-310). Although several growth-promoting bacteria for maize have been selected in the previous years (Garcia et al 2017 Microbiol Res 202:21-29; Li et al. 2017 Int. 1 Mol Sci 18:1253; Oliveira et al. 2017 Front Microbiol 8:1873; Naveed et al 2013 Environ Exper Bot 97:30-39), PGP rhizobacterial strains boosting maize growth under low temperature conditions have not been detected and studied yet.

The rhizosphere is well known to host a variety of plant growth promoting microorganisms. The term "rhizosphere" is used interchangeably with "root zone" to denote that segment of the soil that surrounds the roots of a plant and is influenced by them. In the last decade it has been repeatedly demonstrated that rhizosphere colonizers can also enter plants and that the plant interior (also referred to as "endosphere") is colonized by a range of endophytes mostly deriving from the rhizosphere (Compant et al 2010 Soil Biol Biochem 42: 669-678). Many of those endophytes have been reported to improve plant growth or health. Following rhizosphere colonization endophytes may colonize various plant organs (Compant et al 2010 Soil Biol Biochem 42: 669-678). As a result, distinct microbial communities have been found in various plant organs such as roots, stem, leaves, flowers as well as fruits and seeds or even during plant development indicating different capacities of bacterial strains to colonize various plant compartments (Compant et al 2010 Soil Biol Biochem 42: 669-678).

To identify bacteria that provide cold tolerance to juvenile maize, the inventors of current application first aimed at establishing a main maize root endosphere microbiome consisting of repeatedly enriched and high abundant families in the root microbiome compared to the bulk soil microbiome. Said microbiome was recovered from maize grown both in the field under variable climatic conditions and in pots filled with the same Belgian field soil under controlled growth chamber conditions. The data of the two experiments were compared and resulted in a list of 12 bacterial families. More than half of the families belong to the Proteobacteria phylum: Blrii41, Caulobacteraceae, Comamonadaceae, Hyphomicrobiaceae, Oxalobacteraceae, Rhizobiaceae and Xanthomonadaceae. Five families belonging to other phyla:

Anaerolineaceae, Cytophagaceae, Erysipelotrichaceae, Flavobacteraceae and Streptomycetaceae.

Next, a selection of the obtained maize root endosphere microbiome was screened for growth promotion of maize under low temperature conditions. Comparing growth of inoculated versus non-inoculated seedings surprisingly revealed that inoculation with a *Caulobacter* strain increased the cold tolerance of plants. Phylogenetic analyses (including a 16S rRNA blast) demonstrated that the strain is novel. The highest homology based on 16S rRNA sequence comparisons was found for C. segnis (99.15% homology) and C. vibrioides (99.0%) on species level. On strain level the highest homology could be found with *Caulobacter* sp. FWC28 and FWC31 (99.51%) (Abraham et al 1999 Int J Syst Bacteriol 49:1053-1073). The *Caulobacter* strain herein disclosed is referred to as *Caulobacter* sp. RHG1. Its 16S rRNA sequence is depicted in SEQ ID No. 1.

Further, it could be demonstrated that inoculation of plant seeds with said *Caulobacter* sp. RHG1 strain has also a positive effect on plant growth under optimal temperature conditions. Surprisingly *Caulobacter* sp. RHG1 even increased plant growth under salt stress. Although the art previously disclosed *Caulobacter* vibrioides strain T5M6 as a selenium-solubilizing bacterium that enhances the bioavailability of supplied selenium for plants which positively impacts plant growth, T5M6 does not promote plant growth in the absence of added selenium (CN104498411A). A number of *Caulobacter* isolates have been shown to produce plant growth promoting compounds (Yang et al 2019 Genome Reports 9:42; Pereira et al 2016 Ecol Eng 87:91-97; Chimwamurombe et al 2016 FEMS Microbiol Ecol 92:fiw083), but to the best of Applicant's knowledge, C. segnis nor C. vibrioides have been directly connected with plant growth promotion in the absence of fertilizers. Furthermore, the art is completely silent about a link between *Caulobacter* and tolerance of plants towards cold or salt.

Comparing growth of inoculated versus non-inoculated seedings surprisingly revealed that inoculation with two additional bacterial genera, more precisely *Bosea* and *Pseudoduganella* increased the cold tolerance of plants as well. Phylogenetic analyses (including a 16S rRNA blast) demonstrated that the strains are novel. The *Bosea* strain RHGS disclosed in current application is most closely related to Bosea massiliensis, more precisely a homology of 99.0% on 16S rRNA level. The 16S rRNA sequence of strain RHGS is depicted in SEQ ID No. 2.

The *Pseudoduganella* strain RHG12 disclosed in current application is most closely related to *Pseudoduganella* violaceinigra, more precisely a homology of 99.35% on 16S rRNA level. The 16S rRNA sequence of strain RHG12 is depicted in SEQ ID No. 3.

Based hereon, the invention is further defined in the following aspects and embodiments.

In a first aspect, an isolated bacterial strain comprising a 16S rRNA sequence is provided, wherein said 16S rRNA sequence exhibits at least 99.6% sequence identity to SEQ ID No. 1 or at least 99.2% sequence identity to SEQ ID No. 2 or at least 99.4% sequence identity to SEQ ID No. 3.

In one embodiment, said isolated bacterial strain comprises a 16S rRNA sequence which exhibits at least 99.7%, at least 99.8% or at least 99.9% sequence identity to SEQ ID No. 1. In one particular embodiment, said isolated bacterial strain comprises a 16S rRNA sequence that is identical over the full length thereof to the sequence depicted in SEQ ID No. 1. In another particular embodiment, said isolated bacterial strain is the *Caulobacter* sp. strain RHG1 with deposit number LMG P-31259. In current application it is demonstrated that the plant growth promoting effect of *Caulobacter* strain RHG1 is independent from the plant hormone auxin. Therefore, in a most particular embodiment, the *Caulobacter* strains disclosed herein do not produce the phytohormone indole-3-acetic acid or IAA. In another most particular embodiment, the *Caulobacter* strains disclosed herein are not involved in selenium. This is equivalent as saying that said *Caulobacter* strains do not transform insoluble selenium and selenium mineral into soluble selenium. In yet another embodiment, the *Caulobacter* strains disclosed herein are not involved in heavy metal (copper, zinc, cadmium, cobalt or lead) resistance.

In another embodiment, said isolated bacterial strain comprises a 16S rRNA sequence which exhibits at least 99.2%, at least 99.3%, at least 99.4%, at least 99.5%, at least 99.6%, at least 99.7%, at least 99.8% or at least 99.9% sequence identity to SEQ ID No. 2. In one particular embodiment, said isolated bacterial strain comprises a 16S rRNA sequence that is identical over the full length thereof to the sequence depicted in SEQ ID No. 2. In another particular embodiment, said isolated bacterial strain is the Bosea sp. strain RHGS with deposit number LMG P-31260.

In another embodiment, said isolated bacterial strain comprises a 16S rRNA sequence which exhibits at least 99.4%, at least 99.5%, at least 99.6%, at least 99.7%, at least 99.8% or at least 99.9% sequence identity to SEQ ID No. 3. In one particular embodiment, said isolated bacterial strain comprises a 16S rRNA sequence that is identical over the full length thereof to the sequence depicted in SEQ ID No. 3. In another particular embodiment, said isolated bacterial strain is the *Pseudoduganella* sp. strain RHG12 with deposit number LMG P-31261.

The above described bacterial strains are from here on referred to as "the bacterial strains of current application" and one of said bacterial strains is referred to as "one of the bacterial strains of current application". The bacterial strains of current application are bacteria isolated from the endosphere and are thus living within a plant for at least part of their life without causing apparent disease. Experimental confirmation is provided for the endophytic nature of the isolated *Caulobacter* strain RHG1 in Example 3. These kinds of symbionts are called "endophytes". Endophytes may be transmitted either vertically (directly from parent to offspring) or horizontally (from individual to unrelated individual). Hence, endophytes do not need to have a strictly endophytic life-cycle. They can originate from the rhizosphere and colonize the interior of the plant at a later stage or at a specific stage in their life-cycle. In particular embodiments, said isolated bacterial strains of current application are provided here as endophytes or as endophytic bacterial strains.

The term "isolated" means that the bacterial strain has been removed from its natural environment. "Isolated" thus implies a purification step. However, "isolated" does not necessarily reflect the extent to which the microorganism, more particularly the bacterium has been purified. A bacterial strain of current application is purified at least 2×, at least 5×, at least 10×, at least 50×, or at least 100× from the raw material from which it is isolated. As a non-limiting example, if a microorganism is isolated from soil as raw material, the microorganism can be isolated to an extent that its concentration in a given quantity of purified or partially purified material (e.g. soil) is at least 2×,at least 5×, at least 10×, at least 50×, or at least 100× that in the original raw material.

In one embodiment an enriched culture of one of the bacterial strains of current application is provided. The term "culture" as used herein refers to a population of microorganisms that are propagated on or in media of various kinds. An "enriched culture" of one of the bacterial strains of current application (e.g. *Caulobacter* strain RHG1) refers to a culture of microorganisms, more particular a bacterial culture, wherein the total microbial population of the culture contains more than 50%, more than 60%, more than 70%, more than 80%, more than 90%, or more than 95% of one of the isolated bacterial strains of current application (e.g. *Caulobacter* strain RHG1). This is equivalent as saying that a culture of microorganisms, more particularly a bacterial culture, is provided, wherein said culture is enriched with one of the bacterial strains of current application (e.g. *Caulobacter* strain RHG1) and wherein "enriched" means that the total microbial (or more particularly the total bacterial) population of said culture contains more than 50%, more than 60%, more than 70%, more than 80%, more than 90%, or more than 95% of one of the isolated bacterial strains of current application (e.g. *Caulobacter* strain RHG1).

In another embodiment, a biologically pure culture of one of the bacterial strains of current application is provided. As used herein, "biologically pure" refers to a culture which contains substantially no other microorganisms than the desired strain of microorganism and thus a culture wherein virtually all of the cells present are of the selected strain. In practice, a culture is defined biologically pure if the culture contains at least more than 96%, at least more than 97%, at least more than 98% or at least more than 99% of one of the bacterial strains of current application. When a biologically pure culture contains 100% of the desired microorganism a monoculture is reached. A monoculture thus only contains cells of the selected strain and is the most extreme form of a biologically pure culture.

In yet another embodiment, a supernatant is provided wherein said supernatant is obtained from a culture of at least one of the bacterial strains of current application and wherein said culture can be an enriched culture of said at least one strain or a biologically pure culture of said at least one strain. "Supernatant" refers to the liquid broth remaining when cells grown in broth are removed by centrifugation, filtration, sedimentation or other means well known in the art.

In yet another embodiment, an extract is provided wherein said extract is obtained from a culture of at least one of the bacterial strains of current application wherein said culture can be an enriched culture of said at least one strain or a biologically pure culture of said at least one strain. An "extract" as used herein refers to various forms of microbial products. These products are obtained by removing the cell walls and/or cell membranes of the microorganisms, a process also known as lysis, thereby obtaining one or more endogenous products of the cultured microorganisms. Non-limiting examples of such products are amino acids, peptides, enzymes, secondary metabolites, vitamins, minerals. Removing the cell walls and/or cell membranes of the cultured microorganisms can be obtained by several procedures which are well-known by the person skilled in the art. Non-limiting examples are addition of chemicals (e.g. sodium chloride) to a microbial culture, heating the microbial culture or induce lysis in a mechanical way. An extract can also be obtained by autolysis of the microorganisms.

In yet another embodiment, a composition is provided comprising one of the bacterial strains of current application and an agriculturally compatible carrier. Also a composition is provided wherein said composition comprises one or more products derived from a culture of at least one of the bacterial strains of current application. Said one or more products can be obtained from the supernatant or from an extract of said culture. The term "composition" as used herein is intended to mean a combination of an active agent (for this application this can be one or more of the bacterial strains of the current application, or an extract of its culture, or the supernatant of its culture, or one or more products derived from the said one or more strains of the current application) and at least another compound which can be inert (e.g. a detectable agent or label or liquid carrier) or active (e.g. a fertilizer). Non-limiting examples of said composition in practice are soluble powders, wettable granules, dry flowables, aqueous flowables, wettable dispersible granules, emulsifiable concentrates, aqueous suspensions, a fertilizer granule, a sprayable formulation, an agrochemical formulation. Thus, in another embodiment, an agricultural composition comprising at least one of the bacterial strains of current application is provided. "Agricultural composition" as used herein refers to a composition for agricultural purposes. Given that the composition is of use to promote plant growth and development, also a plant growth promoting composition is provided. Plant growth promoting refers to a promoting effect on the growth and development of the cultured plant or crop. Said cultured plant or crop is the plant or crop of interest and does not include unwanted plants. As such, a "plant growth promoting composition" can include a herbicide, if said herbicide is used to remove unwanted plants. This agricultural or plant growth promoting composition can include a fertilizer, a micronutrient fertilizer material, an insecticide, an herbicide, a plant growth amendment, a fungicide, a molluscicide, an algicide, a bacterial inoculant, a fungal inoculant, or a combination thereof. In some cases, the fertilizer is a liquid fertilizer. Liquid fertilizer can include without limitation, ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, hampene (chelated iron), dolomitic limestone, hydrate lime, calcium carbonate, diammonium phosphate, monoammonium phosphate, potassium nitrate, potassium bicarbonate, monopotassium phosphate, magnesium nitrate, magnesium sulfate, potassium sulfate, potassium chloride, sodium nitrates, magnesian limestone, magnesia, disodium dihydromolybdate, cobalt chlorid hexahydrate, nickel chloride hexahydrate, indole butyric acid, L-tryptophan, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion or a combination thereof. The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate or a combination thereof. In a particular embodiment, said fertilizer or fertilizer material does not comprise insoluble selenium, selenium mineral, soluble selenium or salts thereof. The insecticide can include an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof. The herbicide can comprise a chlorophenoxy compound, a nitrophenolic compound, a nitrocresolic compound, a dipyridyl compound, an acetamide, an aliphatic acide, an anilide, a benzamide, a benzoic acid, a benzoic acid derivative, anisic acid, an anisic acid derivative, a benzonitrile, benzothiadiazinone dioxide, a thiocarbamate, a carmabate, carbanilate, chloropyridinyl, a cyclohexenone derivative, a dinitroaminobenzene derivative, a fluorodinitrotoluidine compound, isoxazolidinone, nicotinic acide, isopropylamine, an isopropulamine derivative, oxadiazolinone, a phosphate, a phthalate, a picolinic acid compound, a triazine, a triazole, a uracil, a urea derivative, endothall, sodium chlorate, or a combination thereof. The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof. The fungal inoculant can comprise a fungal inoculant of the family Glomeraceae, a fungal inoculant of the family Claroidoglomeraceae, a fungal inoculant of the family Acaulosporaceae, a fungal inoculant of the family Sacculospraceae, a fungal inoculant of the family Entrophosporaceae, a fungal inoculant of the family Pacidsproraceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporacea, a fungal inoculant of the family Scutellosproaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, a fungal inoculant of the genus Glomus or a combination thereof. The bacterial inoculant can include a bacterial inoculant of the genus *Rhizobium,* bacterial inoculant of the genus *Bradyrhizobium,* bacterial inoculant of the genus *Mesorhizobium,* bacterial inoculant of the genus *Azorhizobium,* bacterial inoculant of the genus *Allorhizobium,* bacterial inoculant of the genus *Burkholderia,* bacterial inoculant of the genus *Sinorhizobium,* bacterial inoculant of the genus *Kluyvera,* bacterial inoculant of the genus *Azotobacter,* bacterial inoculant of the genus *Pseudomonas,* bacterial inoculant of the genus Azosprillium, bacterial inoculant of the genus *Bacillus,* bacterial inoculant of the genus *Streptomyces,* bacterial inoculant of the genus *Paenibacillus,* bacterial inoculant of the genus *Paracoccus,* bacterial inoculant of the genus Enterobacter, bacterial inoculant of the genus *Alcaligenes,* bacterial inoculant of the genus *Mycobacterium,* bacterial inoculant of the genus Trichoderma, bacterial inoculant of the genus Gliocladium, bacterial inoculant of the genus *Klebsiella,* or a combination thereof. Also, the application provides a combination comprising at least one of the bacterial strains of current application and at least one microorganism selected from the list consisting of *Bacillus subtilis* strain 713, *Bacillus amyloliquefaciens* MBI 600, *Bacillus pumillus* QST2808, *Pseudomonas fluorescens, Bradyrhizobium japonicum,* Trichoderma vireus, Pseudomonas putida, Trichoderma harzianum Rifai strain T22, Penicillium bilaii, *Mesorhizobium, Azospirillum, Azotobacter vinelandii* and *Clostridium pasteurianum.*

In another embodiment, an agricultural or plant growth promoting composition comprising one or more of the bacterial strains of current application and an agriculturally compatible carrier is provided. Also an agricultural or plant growth promoting composition is provided comprising an agriculturally compatible carrier and one or more products derived from a culture of one or more of the bacterial strains of the current application. An "agriculturally compatible carrier" may be a natural or synthetic, organic or inorganic material with which the active compounds (e.g. one of the bacterial strains of the current application or one or more products derived from a culture of said bacterial strain) are combined to facilitate their application into the plant or to the plant growth medium. Said "agriculturally compatible carrier" which can be regarded as a vehicle, is generally inert and it must be acceptable in agriculture. Thus, the phrase "agriculturally compatible" denotes a substance that can be used routinely under field conditions without interfering with growers' planting equipment, and without adversely influencing crop development or the desired ecological balance in a cultivated area.

The agriculturally compatible carrier can be solid. Solid carriers can include but are not limited to clays, natural or synthetic silicates, silica, resins, waxes, solid fertilizers, a polymer, a granular mass, perlite, a perlite granule, peat, a peat pellet, soil, vermiculite, charcoal, sugar factory carbonation press mud, rice husk, carboxymethyl cellulose, fine sand, calcium carbonate, flour, alum, a starch, talc, polyvinyl pyrrolidone, or a combination thereof. The agriculturally compatible carrier can be a liquid. Liquid carriers can include but are not limited to water, alcohols, ketones, petroleum fractions, oils, aromatic or paraffinic hydrocarbons, chlorinated hydrocarbons, liquefied gases or a combination thereof. More particularly, the agriculturally compatible carrier can include a dispersant, a surfactant, an additive, a thickener, an anti-caking agent, residue breakdown, a composting formulation, a granular application, diatomaceous earth, a coloring agent, a stabilizer, a preservative, a polymer, a coating or a combination thereof. One of the ordinary skills in the art can readily determine the appropriate carrier to be used taking into consideration factors such as a particular bacterial strain, plant to which the inoculum is to be applied, type of soil, climate conditions, whether the inoculum is in liquid, solid or powder form, and the like. The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof. The proteinaceous material can include a milk product, wheat flour, soybean meal, blood, albumin, gelatin, or a combination thereof. The thickener can comprise a long chain alkylsulfonate of polyethylene glycol, polyoxyethylene oleate or a combination thereof. The surfactant can contain a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof. The anti-caking agent can include a sodium salt such as a sodium sulfite, a sodium sulfate, a sodium salt of monomethyl naphthalene sulfonate, or a combination thereof; or a calcium salt such as calcium carbonate, diatomaceous earth, or a combination thereof. The agriculturally compatible carrier can also include a fertilizer, a micronutrient fertilizer material, an insecticide, a herbicide, a plant growth amendment, a fungicide, a molluscicide, an algicide, a bacterial inoculant, a fungal inoculant, or a combination thereof. Non-limiting examples are provided above. As way of example, one of the bacterial strains of the current application or the supernatant of its culture or an extract of its culture may be mixed with an agriculturally compatible carrier. In some embodiments, one of the bacterial strains of current application may be lyophilized or freeze-dried to a powder or an aqueous slurry of one of the bacterial strains of the current application may be dried to a powder at a temperature which does not adversely affect viability of the micro-organism. The powder may then be mixed with an agriculturally compatible carrier. In other embodiments, a liquid suspension of one of the bacterial strains of the current application or the supernatant of a culture of said strain may be applied to an absorbent material, e.g. a granular mass, or may be used to coat plant seeds or other plant tissues.

In a second aspect, a plant seed or plant propagule coated with a microbial population comprising at least one of the bacterial strains of current application is provided. This is equivalent as saying that a plant seed or plant propagule is provided, wherein said plant seed or propagule having applied to the surface of said seed or of said propagule, an enriched culture or biological pure culture of one of the bacterial strains of current application.

In one embodiment, said at least one of the bacterial strains of current application is an isolated bacterial strain comprising a 16S rRNA which exhibits at least 99.6% sequence identity to SEQ ID No. 1 or at least 99.2% sequence identity to SEQ ID No. 2 or at least 99.4% sequence identity to SEQ ID No. 3. In another embodiment, said at least one of the bacterial strains of current application is the *Caulobacter* sp. strain RHG1 with deposit number LMG P-31259, or the *Bosea* sp. strain RHGS with deposit number LMG P-31260 or the *Pseudoduganella* sp. strain RHG12 with deposit number LMG P-31261.

In yet another embodiment, when used as a seed treatment, the one of the bacterial strains of current application is applied at a rate of about $1\times10^2$ to about $1\times10^9$ cfu/seed or at a rate of about 133 $10^3$ to about $1\times10^7$ cfu/seed or at a rate of at least $1\times10^2$, at least $1\times10^3$, at least $1\times10^4$, at least $1\times10^5$, at least $1\times10^6$, at least $1\times10^7$, at least $1\times10^8$ or at least $1\times10^9$ cfu/seed. In yet another embodiment, for coating purposes seeds are treated with a bacterial solution of at least $1\times10^5$ cfu of one of the bacterial strains of current application per ml, at least $1\times10^6$ cfu of one of the bacterial strains of current application per ml, at least $1\times10^7$ cfu of one of the bacterial strains of current application per ml, at least $1\times10^8$ cfu of one of the bacterial strains of current application per ml, at least $1\times10^9$ cfu of one of the bacterial strains of current application per ml, at least $1\times10^{10}$ cfu of one of the bacterial strains of current application per ml or at least $1\times10^{11}$ cfu of one of the bacterial strains of current application per ml. "CFU" or "cfu" as used herein refers to colony-forming unit. This unit is well-known by the person skilled in the art of microbiology (as well as the methodology how to determine the number of colony-forming units) and is used to estimate the number of viable bacteria or fungal cells in a sample. "Viable" is defined as the ability to multiply via binary fission under controlled conditions. Counting with colony-forming units requires culturing the microbes and counts only viable cells, in contrast with microscopic examination which counts all cells, living or dead.

A "plant propagule" is any plant material for the purpose of plant propagation. Because of the totipotency of plants, any part of the plant may be used (e.g. a stem cutting, a leaf section, a portion of a root), though it is usually a highly meristematic part such as root and stem ends, buds, tubers, bulbs, rhizome, stolon or any plant part for vegetative reproduction. In sexual reproduction, a propagule is a seed or spore.

A "plant seed coated" or alternatively a "coated seed" as used in this application refers to a plant seed covered with a certain composition. This composition (i.e. the coating composition) can be a water composition or an oil composition or a polymer. "Coating" includes the most simple covering methods of dipping seeds or plant propagules in a microbial suspension or spraying seeds or propagules with a microbial suspension. In the latter case, the coating compositions are found to be film-forming, i.e., upon contacting with seeds or propagules they form a thin liquid film that adheres to the surface. "Coating" also includes rolling seeds/propagules in or dusting seeds/propagules with or brushing seeds/propagules with a powder comprising microorganisms, to more complex procedures as injecting plant seeds/propagules with a composition comprising microorganism or the use of complex coating layers including one or more adhesive, binder solvent and/or filler components. A person skilled in the art is familiar with a variety of conventional and more advanced methods to coat plants seeds (e.g. US5113619, EP0080999, WO1997036471, EP0010630, WO2006131213, WO2001045489, US4465017, EP2676536 which are here all incorporated as reference). The coating composition can include a number of ingredients, including but not limited to gelatin, a desiccant, water, tallow (e.g. to increase the release rate of any active ingredient in the composition), bulking agents (e.g. clay, and bentonite to give more body to the liquid coating composition). Coating compositions which include bulking agents produce more rounded coated seeds. Such coated seeds are generally easier to plant when using mechanical planters. The concentration of the bulking agent can be up to about 50% of the solids by volume. As way of example of a liquid coating procedure, seeds or propagules are fed into one or more tanks containing the liquid coating composition. The seeds or propagules are transported from the tanks into a drying zone where forced air dries and solidifies the coating applied to the seeds. The seeds or propagules are dipped at least once and preferably at least twice in the liquid coating composition of the present invention. The dried coated seeds or propagules can be sowed or planted using standard sowing or planting machinery or by hand. In the alternative, the coated seeds or propagules can be stored for later application. If the temperature and humidity are relatively high or if prolonged storage is contemplated, it is desirable to place on the surface of the coating an inert material, preferably a powder material, such as, chalk or talcum powder. Such inert material reduces the tendency for the seed to stick together or agglomerate. The coating should cover more than 50%, more than 60%, more than 70%, more than 80%, more than 90, more than 95% of the surface area of the seeds or propagules. In some embodiments, after the coating procedure, the seeds should comprise at least one living cell of one of the isolated bacterial strains of current application. In other embodiments, after the coating procedure, the seeds should comprise at least an effective amount of one or more extracts of a culture of one of the bacterial strains of current application. The coating layer can also consist of one or more components. These components can be additional plant growth promoting microorganisms but can also be fertilizers, biocontrol agents, or pesticides including fungicides, insecticides and herbicides. Non-limiting examples of these components are provided above. The coating composition can also include protective colloids, adhesives, thickening agents, thixotropic agents, penetrating agents, stabilizing agents, sequestering agents, fertilizers, anti-freeze agents, repellents, color additives, corrosion inhibitors, water-repelling agents, siccatives, UV-stabilizers, pigments, dyes or polymers. “Population” as used in this application refers to a group or collection of organisms. These organisms can but don’t have to be part of the same species and do not need to originate from the same geographical area and do not need to have the capability of interbreeding. “Microbial” as used herein refers to microorganisms, wherein said microorganisms can include bacteria, archaebacteria, fungi, yeasts, mycorrhiza, microscopic eukaryotes (e.g. protozoa and algae), viruses, viroids or a combination thereof. A “microbial population” as used herein can thus refer to a synthetic or artificial collection of different microorganisms with distinct geographical origins. In various more particular embodiments of this application, “microbial” refers to “bacterial”.

In a third aspect, the use of a microbial population comprising at least one of the bacterial strains of current application is provided to increase or improve yield, growth, cold tolerance and/or salt tolerance of plants, wherein said at least one of the bacterial strains of current application comprises a 16S rRNA sequence exhibiting at least 99.6% sequence identity to SEQ ID No. 1 or at least 99.2% sequence identity to SEQ ID No. 2 or at least 99.4% sequence identity to SEQ ID No. 3.

In one embodiment, said use is provided wherein said at least one of the bacterial strains of current application is the *Caulobacter sp. strain RHG*1 with deposit number LMG P-31259, or the *Bosea* sp. strain RHGS with deposit number LMG P-31260 or the *Pseudoduganella* sp. strain RHG12 with deposit number LMG P-31261.

In a most particular embodiment, the plant growth promoting effect of one of the *Caulobacter* strains disclosed in current application does not depend on the production of the phytohormone indole-3-acetic acid by said *Caulobacter* strain.

In various embodiments of this third aspect, the increase or improvement is an at least 5% increase or at least 6% increase or at least 7% increase or at least 8% increase or at least 9% increase or at least 10% increase or at least 15% increase or at least 20% or at least 25% or at least 30% or at least 50% increase or at least 75% increase or at least a 100% increase in the property being measured and compared to a control situation. Said control situation is a mock situation wherein the plant, plant seed or other plant part was not treated with the microbial population or bacterial strain. The skilled person is aware how a scientifically sound mock situation should be set up. “Treated” as used herein can be direct treatment (e.g. coating seeds or spraying plants) and/or indirect treatment (e.g. providing the substrate wherein the plant is growing with a bacterial population). As non-limiting examples, the microbial population comprising one of the bacterial strains of the current application may produce an above stated increase in total fresh plant weight, or in fresh shoot weight, or in fresh root weight, or in leaf area or in plant product yield, or an above stated percentage increased accumulated biomass of the plant or an above stated percentage increase in number of tillers.

Thus in a more particular embodiment, a microbial population comprising one of the bacterial strains of current application is provided to enhance or increase plant yield. “Yield” as used herein, generally refers to a measurable product from a plant, and more particularly to the amount of harvestable plant material or plant-derived product. “Yield” is normally defined as the measurable produce of economic value of a crop. For crop plants, “yield” also means the amount of harvested material per hectare or unit of production. Yield may be defined in terms of quantity or quality. The harvested material may vary from crop to crop, for example, it may be seeds, above ground biomass, roots, fruits, cotton fibres, any other part of the plant, or any plant-derived product which is of economic value. The term “yield” also encompasses yield potential, which is the maximum obtainable yield. Yield may be dependent on a number of yield components, which may be monitored by certain parameters. These parameters are well known to persons skilled in the art and vary from crop to crop. The yield can be determined using any convenient method, for example, kilograms of plant product produced per hectare of planting or bushels or pound of plant product produced per acre of planting. The term “yield” also encompasses harvest index, which is the ratio between the harvested biomass over the total amount of biomass. Yield and yield increase (in comparison to a control plant) can be measured in a number of ways, and it is understood that a skilled person will be able to apply the correct meaning in view of the particular embodiments, the particular crop concerned and the specific purpose or application concerned. The terms “enhanced yield” or “improved yield” or “increased yield” can be used interchangeable. As used herein, the term “enhanced yield” means any improvement in the yield of any measured plant product, such as grain, fruit, leaf, root, cob or fiber. In accordance with the invention, changes in different phenotypic traits may improve yield. For example, and without limitation, parameters such as floral organ development, root initiation, root biomass, seed number, seed weight, harvest index, leaf formation, phototropism, apical dominance, and fruit development, are suitable measurements of improved yield. Increased yield includes higher fruit yields, higher seed yields, higher fresh matter production, and/or higher dry matter production. Any increase in yield is an improved yield in accordance with the invention. For example, the improvement in yield can comprise a 0.1%, 0.5%, 1%, 3%, 5%, 10%, 15%, 20%, 30%, 40%, 50%, 60%, 70%, 80%, 90% or greater increase in any measured parameter compared to a mock situation (see above). For example, an increase in the bushels/acre yield of wheat or corn derived from a crop comprising plants which are treated with the plant growth promoting bacteria of the invention, as compared with the bushels/acre yield from untreated wheat or corn cultivated under the same conditions, is an improved yield in accordance with the invention. The increased or improved yield can be achieved in the absence or presence of stress conditions. For example, enhanced or increased “yield” refers to one or more yield parameters selected from the group consisting of biomass yield, dry biomass yield, aerial dry biomass yield, underground dry biomass yield, fresh-weight biomass yield, aerial fresh-weight biomass yield, underground fresh-weight biomass yield; enhanced yield of harvestable parts, either dry or fresh-weight or both, either aerial or underground or both; enhanced yield of crop fruit, either dry or fresh-weight or both, either aerial or underground or both; and enhanced yield of seeds, either dry or fresh-weight or both, either aerial or underground or both. “Crop yield” is defined herein as the number of bushels of relevant agricultural product (such as grain, forage, or seed) harvested per acre. Crop yield is impacted by abiotic stresses, such as drought, heat, salinity, and cold stress, and by the size (biomass) of the plant. The yield of a plant can depend on the specific plant/crop of interest as well as its intended application (such as food production, feed production, processed food production, biofuel, biogas or alcohol production, or the like) of interest in each particular case. Thus, in one embodiment, yield can be calculated as harvest index (expressed as a ratio of the weight of the respective harvestable parts divided by the total biomass), harvestable parts weight per area (acre, square meter, or the like); and the like. The harvest index is the ratio of yield biomass to the total cumulative biomass at harvest. Harvest index is relatively stable under many environmental conditions, and so a robust correlation between plant size and grain yield is possible. Measurements of plant size in early development, under standardized conditions in a growth chamber or greenhouse, are standard practices to measure potential yield advantages conferred by the presence of plant growth promoting bacteria. Accordingly, the yield of a plant can be increased by improving one or more of the yield-related phenotypes or traits. Such yield-related phenotypes or traits of a plant the improvement of which results in increased yield comprise, without limitation, the increase of the intrinsic yield capacity of a plant, improved nutrient use efficiency, and/or increased stress tolerance.

For example, yield refers to biomass yield, e.g. to dry weight biomass yield and/or fresh-weight biomass yield. Biomass yield refers to the aerial or underground parts of a plant, depending on the specific circumstances (test conditions, specific crop of interest, application of interest, and the like). In one embodiment, biomass yield refers to the aerial and underground parts. Biomass yield may be calculated as fresh-weight, dry weight or a moisture adjusted basis. Biomass yield may be calculated on a per plant basis or in relation to a specific area (e.g. biomass yield per acre/square meter/or the like). “Yield” can also refer to seed yield which can be measured by one or more of the following parameters: number of seeds or number of filled seeds (per plant or per area (acre/square meter/or the like)); seed filling rate (ratio between number of filled seeds and total number of seeds); number of flowers per plant; seed biomass or total seeds weight (per plant or per area (acre/square meter/or the like); thousand kernel weight (TKW; extrapolated from the number of filled seeds counted and their total weight; an increase in TKW may be caused by an increased seed size, an increased seed weight, an increased embryo size, and/or an increased endosperm). Other parameters allowing to measure seed yield are also known in the art. Seed yield may be determined on a dry weight or on a fresh weight basis, or typically on a moisture adjusted basis, e.g. at 15.5% moisture. For example, the term “increased yield” means that a plant, exhibits an increased growth rate, e.g. in the absence or presence of abiotic environmental stress, compared to the corresponding wild-type plant. An increased growth rate may be reflected inter alia by or confers an increased biomass production of the whole plant, or an increased biomass production of the aerial parts of a plant, or by an increased biomass production of the underground parts of a plant, or by an increased biomass production of parts of a plant, like stems, leaves, blossoms, fruits, and/or seeds. A prolonged growth comprises survival and/or continued growth of the plant, at the moment when the untreated control plant shows visual symptoms of deficiency and/or death. When the plant treated with one of the plant growth promoting bacterial strains of the application is a corn plant, increased yield for corn plants means, for example, increased seed yield, in particular for corn varieties used for feed or food. Increased seed yield of corn refers to an increased kernel size or weight, an increased kernel per ear, or increased ears per plant. Alternatively or in addition the cob yield may be increased, or the length or size of the cob is increased, or the kernel per cob ratio is improved. When the plant treated with one of the plant growth promoting bacterial strains of the application is wheat, increased yield for wheat means, for example, increased seed yield. Increased seed yield of wheat refers to an increased kernel size, an increased kernel filling, increased thousand kernel weight, an increased kernel per ear, an increased grain yield per plant, or increased ears per plant. Alternatively or in addition the ear yield may be increased, or the length or size of the ear is increased, or the seeds per ear ratio is improved. When the plant treated with one of the bacterial strains of the application is a soy plant, increased yield for soy plants means increased seed yield, in particular for soy varieties used for feed or food. Increased seed yield of soy refers for example to an increased kernel size or weight, an increased kernel per pod, or increased pods per plant. When the plant treated with one of the bacterial strains of the application is an oil seed rape (OSR) plant, increased yield for OSR plants means increased seed yield, in particular for OSR varieties used for feed or food. Increased seed yield of OSR refers to an increased seed size or weight, an increased seed number per silique, or increased siliques per plant. When the plant treated with of the plant growth promoting bacterial strains of the application is a cotton plant, increased yield for cotton plants means increased lint yield. Increased lint yield of cotton refers in one embodiment to an increased length of lint. When the plant treated with one of the plant growth promoting bacterial strains of the application is a plant belonging to grasses an increased leaf can mean an increased leaf biomass. Said increased yield can typically be achieved by enhancing or improving, one or more yield-related traits of the plant. Such yield-related traits of a plant comprise, without limitation, the increase of the intrinsic yield capacity of a plant, improved nutrient use efficiency, and/or increased stress tolerance, in particular increased abiotic stress tolerance. Intrinsic yield capacity of a plant can be, for example, manifested by improving the specific (intrinsic) seed yield (e.g. in terms of increased seed/grain size, increased ear number, increased seed number per ear, improvement of seed filling, improvement of seed composition, embryo and/or endosperm improvements, or the like); modification and improvement of inherent growth and development mechanisms of a plant (such as plant height, plant growth rate, pod number, pod position on the plant, number of internodes, incidence of pod shatter, efficiency of nodulation and nitrogen fixation, efficiency of carbon assimilation, improvement of seedling vigour/early vigour, enhanced efficiency of germination (under stressed or non-stressed conditions), improvement in plant architecture, cell cycle modifications, photosynthesis modifications, various signaling pathway modifications, modification of transcriptional regulation, modification of translational regulation, modification of enzyme activities, and the like); and/or the like.

In a more particular embodiment, a microbial population comprising one of the bacterial strains of current application is provided to enhance plant yield and/or plant growth in the absence of plant disease. Signs and symptoms of plant disease can be evaluated and interpreted by a person skilled in the art of plant pathology. Practitioners are particularly directed to Westcott's Plant Disease Handbook (R. Kenneth Horst, Springer Netherlands, $8^{th}$ edition, 2013). Non-limiting examples of plant disease symptoms and signs are spots on leaves or on fruit, aberrant coloring of leaves, rot of leaves or fruit or roots, shoot or leaf blight, wilting, and presence of gals or tumors.

In an even more particular embodiment, a microbial population comprising one of the bacterial strains of current application is provided to enhance plant yield and/or plant growth in the absence of pathogen pressure or in the absence of phytopathogenic organisms and/or pest organisms. “Phytopathogenic organisms” as used herein refer to organisms that cause plant disease and include fungi, oomycetes, bacteria, viruses, virus-like organisms, phytoplasmas, protozoa, nematodes and parasitic plants. “Pest organisms” as used herein are organisms that negatively affect plant health by e.g. consumption of plant tissue. Non-limiting examples of pest organisms are insects, mites, gastropods, vertebrates. The term “absence of pathogen pressure and/or pest organisms” as used in current application refers to a situation that does not significantly inhibit plant growth and/or yield. “Significantly inhibiting” as used herein means a reduction of plant growth and/or plant yield of at least 50%, at least 20%, at least 10% or at least 5% compared to a control plant that is not affected by disease and/or pathogen pressure and/or pest organisms.

In other particular embodiments, the use of the *Caulobacter* strain disclosed herein is provided to enhance plant yield and/or plant growth in the absence of selenium or more particularly in the absence of an insoluble form of selenium such as selenium mineral or in the absence of heavy metals such as copper, zinc, cadmium, cobalt or lead.

In yet another embodiment, the use of a microbial population comprising one of the bacterial strains of the application is provided to increase cold tolerance of a plant. This solution is of great agricultural importance as low temperatures often significantly affect plant growth and crop productivity with crop losses as result (Xin and Browse 2001 Plant Cell Environ 23:893-902). Cold tolerance in plants is a very complex trait, involving many different metabolic pathways and cell compartments. Plants respond with changes in their pattern of gene expression and protein products when exposed to low temperatures. Plants differ in their tolerance to cold or chilling (0-17° C.) and freezing (<0° C.) temperatures. Plants of tropical and subtropical origins (e.g. maize) are highly sensitive to cold or chilling stress and are injured or killed by non-freezing low temperatures. They exhibit various symptoms of chilling injury such as chlorosis, necrosis, or growth retardation. In contrast, plants from temperate climatic regions can be cold or chilling tolerant with variable degree and can be able to grow at such non-freezing cold temperatures.

“Cold tolerance” or equivalently “chilling tolerance” or “low temperature tolerance” as used in current application is defined as the ability of a plant to tolerate low temperatures without or with limited injury or damage, wherein said low temperatures are non-freezing temperatures. In one embodiment said low temperatures are temperatures between 0 and 17° C. or between 5 and 17° C. or between 8 and 17° C. or between 12 and 17° C. Plants are exposes to said low temperatures for at least 2 h, at least 4h, at least 6 h or at least 8 h per day or said low temperature are reached during at least a part of the day, for example during the night. In particular embodiments, cold tolerance observed in plants that were treated with or were grown from seeds coated with at least one of the bacterial strains of current application leads to injury or damage due to low temperatures which is at least 10%, least 20%, least 30%, least 40%, least 50%, least 60%, least 70%, least 80%, least 90% or 100% less than the injury or damage observed in plants that were not treated with or were grown from seeds not coated with at least one of the bacterial strains of current application.

In particular embodiments, the use of a bacterial strain comprising a 16S rRNA sequence exhibiting at least 99.6% sequence identity to SEQ ID No. 1 or at least 99.2% sequence identity to SEQ ID No. 2 or at least 99.4% sequence identity to SEQ ID No. 3 is provided to increase tolerance to non-freezing low temperatures in plants, wherein said low temperatures are between 5 and 17° C. or between 10 and 17° C. or between 12 and 17° C.

In one further embodiment, said use is provided wherein said bacterial strain is the *Caulobacter* sp. strain RHG1 with deposit number LMG P-31259, or the *Bosea* sp. strain RHG5 with deposit number LMG P-31260 or the *Pseudoduganella* sp. strain RHG12 with deposit number LMG P-31261.

In yet other embodiments, the use of a microbial population comprising one of the bacterial strains of the application is provided to increase salt tolerance of a plant. Almost all crops that are important to humans are sensitive to high salt concentration in the soil. The presence of salt in soil is one of the most significant abiotic stresses in farming. Therefore, improving plant salt tolerance and increasing the yield and quality of crops in salty land is vital. Salt stress has a significant effect on plant growth and development. Under salt treatment, the seed germination, root length, plant height, and fructification of plant are significantly inhibited (Liang et al 2014 Biochem Bioph Res 450:794-801). Osmotic stress is the first stress experienced when a plant is exposed to saline soil. Water and nutrients from the soil cannot move into the plant roots anymore which instantly affects plant growth (Horie et al 2011 Plant Cell Physiol 52:663-675). Ion toxicity occurs later when salt levels reach a threshold, beyond which the plant cannot maintain ion homeostasis and growth (Munns and Tester 2008 Annu Rev Plant Biol 59:651-681). Ion toxicity and osmotic stress are primary stresses that can cause oxidative stress and a series of secondary stresses. Salt stress also leads to a decrease in photosynthesis (Munns et al 2006 J Exp Bot 57:1025-1043) and results in a substantial decrease of crop yield worldwide (Rengasamy 2010 Funct Plant Biol 37:613-620).

Plant species vary in how well they tolerate salt-affected soils. Some plants will tolerate high levels of salinity while others can tolerate little or no salinity. The relative growth of plants in the presence of salinity is termed their salt tolerance. More particularly for current application, plants that were treated with or were grown from seeds coated with at least one of the bacterial strains of current application are considered salt tolerant if they show at least 10%, least 20%, least 30%, least 40%, least 50%, least 60%, least 70%, least 80%, least 90% or 100% less injury compared to plants that were not treated with or were grown from seeds not coated with at least one of the bacterial strains of current application. In particular embodiments, said injury is determined in the presence of at least 25 mM, at least 50mM, at least 100 mM, at least 150mM salt or between 50 and 200 mM or between 80 and 150 mM salt. In even more particular embodiments, said salt is NaCl and said salt tolerance is tolerance towards a NaCl concentration between 80 mM and 150 mM or between 100 mM and 180 mM.

In a fourth aspect, a method is provided for enhancing growth, yield, cold tolerance and/or salt tolerance of a plant comprising inoculating a plant growth medium with a microbial population, wherein said population comprises at least one of the bacterial strains of current application; and growing a plant in said plant growth medium; to enhance growth, yield, cold tolerance and/or salt tolerance of said plant. In one embodiment, said at least one of the bacterial strains of current application comprises a 16S rRNA sequence exhibiting at least 99.6% sequence identity to SEQ ID No. 1 or at least 99.2% sequence identity to SEQ ID No. 2 or at least 99.4% sequence identity to SEQ ID No. 3. In a particular embodiment, said method is provided wherein said strain is the *Caulobacter* sp. strain RHG1 with deposit number LMG P-31259, or the *Bosea* sp. strain RHG5 with deposit number LMG P-31260 or the *Pseudoduganella* sp. strain RHG12 with deposit number LMG P-31261.

The term "inoculating" as used herein refers to introducing at least one bacterium into a plant growth medium. By way of example and without the intention to be limiting, said introduction can be performed using a liquid, a powder, a granule, a pellet. "Plant growth medium" is defined as any environment wherein plants can grow. Non-limiting examples of a plant growth medium are soil, sand, gravel, a polysaccharide, mulch, compost, peat moss, straw, logs, clay, or a combination thereof. A plant growth medium can also include a hydroculture system as in Example 5 or an in vitro culture system. Hydroculture is the growing of plants in a soilless medium or an aquatic based environment, while an in vitro culture system refers to the growing of plants or explants on or in a recipient with synthetic medium, in sterile conditions, in a controlled environment and in reduced space. Explants refer to parts of a plant, from all the aerial part to isolated cells, as parts of leaves, of roots, seeds, bulbs, tubers, buds. The inoculation of said plant growth medium with a microbial population can be done before, during and/or after sowing or before, during and/or after the start of the plant growth cycle in case of hydroculture or in vitro culture. The inoculation can be performed once or multiple times during the plant growth cycle. The application also envisages the inoculation of the plant growth medium with the supernatant or with an extract of the bacterial culture comprising one of the bacterial strains of current application.

In these and further aspects and embodiments, the term "plant" encompasses whole plants and plant parts, including seeds, shoots, stems, leaves, roots (including tubers), bulbs, buds, flowers, and tissues and organs. The term "plant" also encompasses plant cells, suspension cultures, callus tissue, embryos, meristematic regions, gametophytes, sporophytes, pollen and microspores. Thus, in one embodiment, a method is provided for stimulating plant growth comprising applying the microbial culture comprising one of the bacterial strains of current application to a plant, plant part, plant seed or to the plant growth medium. In the latter and further embodiments and aspects, "stimulating", "enhancing", "increasing" or "improving" refers to an at least 5% increase or at least 6% increase or at least 7% increase or at least 8% increase or at least 9% increase or at least 10% increase or at least 12% increase or at least 15% increase or at least 20% increase or at least 25% increase or at least 30% increase or at least 50% increase or at least 75% increase or at least a 100% increase in the property being measured (e.g. plant growth, plant yield) and compared to a mock or control situation.

Plants that are particularly useful in the methods of current application include in particular monocotyledonous and dicotyledonous plants including fodder or forage legumes, ornamental plants, food crops, trees or shrubs selected from the list comprising Acer spp., Actinidia spp., Abelmoschus spp., Agave sisalana, Agropyron spp., Agrostis stolonifera, Allium spp., Amaranthus spp., Ammophila arenaria, Ananas comosus, Annona spp., Apium graveolens, Arachis spp, Artocarpus spp., Asparagus officinalis, Avena spp. (e.g. Avena sativa, Avena fatua, Avena byzantina, Avena fatua var. sativa, Avena hybrida), Averrhoa carambola, Bambusa sp., Benincasa hispida, Bertholletia excelsea, Beta vulgaris, Brassica spp. (e.g. Brassica napus, Brassica rapa ssp. [canola, oilseed rape, turnip rape]), Cadaba farinosa, Camellia sinensis, Canna indica, Cannabis sativa, Capsicum spp., Carex elata, Carica papaya, Carissa macrocarpa, Carya spp., Carthamus tinctorius, Castanea spp., Ceiba pentandra, Cichorium endivia, Cinnamomum spp., Citrullus lanatus, Citrus spp., Cocos spp., Coffea spp., Colocasia esculenta, Cola spp., Corchorus sp., Coriandrum sativum, Corylus spp., Crataegus spp., Crocus sativus, Cucurbita spp., Cucumis spp., Cynara spp., Daucus carota, Desmodium spp., Dimocarpus longan, Dioscorea spp., Diospyros spp., Echinochloa spp., Elaeis (e.g. Elaeis guineensis, Elaeis oleifera), Eleusine coracana, Eragrostis tef, Erianthus sp., Eriobotrya japonica, Eucalyptus sp., Eugenia uniflora, Fagopyrum spp., Fagus spp., Festuca arundinacea, Ficus carica, Fortunella spp., Fragaria spp., Ginkgo biloba, Glycine spp. (e.g. Glycine max, Soja hispida or Soja max), Gossypium hirsutum, Helianthus spp. (e.g. Helianthus annuus), Hemerocallis fulva, Hibiscus spp., Hordeum spp. (e.g. Hordeum vulgare), Ipomoea batatas, Juglans spp., Lactuca spp. (e.g. Lactuca sativa), Lathyrus spp., Lens culinaris, Linum usitatissimum, Litchi chinensis, Lotus spp., Luffa acutangula, Lupinus spp., Luzula sylvatica, Lycopersicon spp. (e.g. Lycopersicon esculentum, Lycopersicon lycopersicum, Lycopersicon pyriforme), Macrotyloma spp., Malus spp., Malpighia emarginata, Mammea americana, Mangifera indica, Manihot spp., Manilkara zapota, Medicago sativa, Melilotus spp., Mentha spp., Miscanthus sinensis, Momordica spp., Morus nigra, Musa spp., Nicotiana spp., Olea spp., Opuntia spp., Ornithopus spp., Oryza spp. (e.g. Oryza sativa, Oryza latifolia), Panicum miliaceum, Panicum virgatum, Passiflora edulis, Pastinaca sativa, Pennisetum sp., Persea spp., Petroselinum crispum, Phalaris arundinacea, Phaseolus spp., Phleum pratense, Phoenix spp., Phragmites australis, Physalis spp., Pinus spp., Pistacia vera, Pisum spp., Poa spp., Populus spp., Prosopis spp., Prunus spp., Psidium spp., Punica granatum, Pyrus communis, Quercus spp., Raphanus sativus, Rheum rhabarbarum, Ribes spp., Ricinus communis, Rubus spp., Saccharum spp., Salix sp., Sambucus spp., Secale cereale, Sesamum spp., Sinapis sp., Solanum spp. (e.g. Solanum tuberosum, Solanum integrifolium or Solanum lycopersicum), Sorghum bicolor, Spinacia spp., Syzygium spp., Tagetes spp., Tamarindus indica, Theobroma cacao, Trifolium spp., Tripsacum dactyloides, Triticosecale rimpaui, Triticum spp. (e.g. Triticum aestivum, Triticum durum, Triticum turgidum, Triticum hybernum, Triticum macha, Triticum sativum, Triticum monococcum or Triticum vulgare), Tropaeolum minus, Tropaeolum majus, Vaccinium spp., Vicia spp., Vigna spp., Viola odorata, Vitis spp., Zea mays, Zizania palustris, Ziziphus spp., amongst others.

In one embodiment of the fourth aspect, the microbial population is applied to the plant growth medium as a powder, as a pellet, as a granule or as a liquid.

In a fifth aspect, a method for enhancing growth, yield, cold tolerance and/or salt tolerance of a plant is provided, wherein said method comprising growing coated seeds of a plant, wherein said seeds are coated with a microbial population comprising one of the isolated bacterial strains of current application, to obtain enhanced growth, yield, cold tolerance and/or salt tolerance of said plant. In some embodiments, after the coating procedure, the seeds should comprise at least one living cell of one of the isolated bacterial strains of current application. In other embodiments, after the coating procedure, the seeds should comprise at least an effective amount of one or more extracts of a culture of one of the bacterial strains of current application. Thus, this application also provides a method for enhancing plant growth and/or plant yield, said method comprising growing coated seeds of a plant, wherein said seeds are coated with an effective amount of an extract of a bacterial population comprising one of the bacterial strains of current application, to obtain enhanced growth, yield, cold tolerance and/or salt tolerance of said plant. This is equivalent as saying that a method is provided for enhancing growth, yield, cold tolerance and/or salt tolerance of a plant, said method comprising germinating seeds of said plant, wherein said seeds are coated with an effective amount of an extract of a bacterial population comprising one of the bacterial strains of current application, to obtain enhanced growth, yield, cold tolerance and/or salt tolerance of said plant.

An "effective amount" refers to an amount sufficient to effect beneficial or desired results. In a non-limiting example, an "effective amount" leads to a statistically significant increase of plant growth and/or biomass and/or yield and/or cold tolerance and/or salt tolerance as compared to the growth, biomass and/or yield and/or cold tolerance and/or salt tolerance of the control plant. An effective amount can be administered in one or more administrations. A "control plant" as used in current application provides a reference point for measuring changes in phenotype of the subject plant and may be any suitable plant cell, seed, plant component, plant tissue, plant organ or whole plant. A control plant may comprise for example a plant or cell which is genetically identical to the subject plant or cell but which is not exposed to the same treatment (e.g. administration of one of the bacterial strains of current application) as the subject plant or cell.

In another embodiment, a method is provided for enhancing nutrient uptake and/or nutrient use efficiency of a plant, said method comprising growing coated seeds of a plant, wherein said seeds are coated with a microbial population comprising one of the bacterial strains of current application, to obtain enhanced nutrient uptake and/or nutrient use efficiency of said plant. In another embodiment, a method is provided for enhancing the nitrogen fixating capacities of a plant, said method comprising growing coated seeds of a plant, wherein said seeds are coated with a microbial population comprising one of the bacterial strains of current application, to obtain enhanced nitrogen fixating capacities of said plant. In alternative embodiments, the current application also envisages that the plant seeds described in the embodiments of the fifth aspect, are coated with an extract of a bacterial culture of one of the bacterial strains of current application instead of with said bacterial population itself. Also, in other alternative embodiments, it is envisaged that the plant seeds described in the embodiments of the fifth aspect, are coated with the supernatant of a bacterial culture of one of the bacterial strains of current application instead of with said bacterial population itself.

In a sixth aspect, a method for enhancing growth, yield, cold tolerance and/or salt tolerance of a plant is provided comprising:

growing a plant in an environment that supports plant growth; and administering a sprayable formulation to said environment or to said plant, said formulation comprising at least one of the bacterial strains of current application;

to obtain enhanced growth, yield, cold tolerance and/or salt tolerance of said plant. In one embodiment, said at least one of the bacterial strains of current application comprises a 16S rRNA sequence exhibiting at least 99.6% sequence identity to SEQ ID No. 1 or at least 99.2% sequence identity to SEQ ID No. 2 or at least 99.4% sequence identity to SEQ ID No. 3. In a particular embodiment, said method is provided wherein said strain is the *Caulobacter* sp. strain RHG1 with deposit number LMG P-31259, or the *Bosea* sp. strain RHGS with deposit number LMG P-31260 or the *Pseudoduganella* sp. strain RHG12 with deposit number LMG P-31261.

A "sprayable formulation" as used herein is an agrochemical or a biological solution that can be sprinkled on a plant or soil. The formulation is composed in such a way that the active ingredients can be absorbed by the above-ground tissue of a plant or is available for the plant roots when administered to the soil. The above disclosed methods thus also includes irrigation with a liquid comprising one of the bacterial strains of current application. "Irrigating" or "irrigation" as used herein refers to the method in which water or other liquids are supplied to plants at regular intervals. Irrigation includes but is not limited to "localized irrigation" (i.e. a system where water is distributed under pressure through a piped network, in a pre-determined pattern, and applied as a small discharge to each plant or adjacent to it. "Drip (or micro) irrigation", also known as "trickle irrigation" (i.e. a system where water falls drop by drop just at the position of roots or near the root zone of plants) and "sprinkler irrigation" (i.e. a system where water is distributed by overhead sprinklers) belong to this category of irrigation methods. In "sprinkler irrigation", sprinklers can also be mounted on moving platforms connected to the water source by a hose. Automatically moving wheeled systems known as traveling sprinklers may irrigate areas such as small farms, sports fields, parks, pastures, and cemeteries unattended. Most of these utilize a length of polyethylene tubing wound on a steel drum. As the tubing is wound on the drum powered by the irrigation water or a small gas engine, the sprinkler is pulled across the field. When the sprinkler arrives back at the reel the system shuts off. This type of system is known to most people as a "waterreel" traveling irrigation sprinkler.

Hence, in various embodiments, a method is provided for enhancing growth, yield, cold tolerance and/or salt tolerance of a plant, said method comprising:

growing said plant in an environment that supports plant growth;

irrigating said environment using a liquid solution comprising one of the bacterial strains of current application;

to obtain enhanced growth, yield, cold tolerance and/or salt tolerance of said plant. In particular embodiments, when used as a soil treatment, the one of the bacterial strains of current application can be applied as a soil surface drench, injected and/or applied in-furrow or by mixture with irrigation water. The rate of application for drench soil treatments, which may be applied at planting, during or after seeding, or after transplanting and at any stage of plant growth, is about $1\times10^{11}$ to about $8\times10^{12}$ cfu per acre. In some embodiments, the rate of application is about $1\times10^{12}$ to about $8\times10^{12}$ cfu per acre. The rate of application for in-furrow treatments, applied at planting, is about $2.5\times10^{10}$ to about $5\times10^{11}$ cfu per 1000 row feet. In some embodiments, the rate of application is about $6\times10^{10}$ to about $4\times10^{11}$ cfu per 1000 row feet. Those of skill in the art will understand how to adjust rates for broadcast treatments (where applications are at a lower rate but made more often) and other less common soil treatments.

In some embodiments, when one of the bacterial strains of current application is applied as microbial population or bacterial population or solution or culture or agricultural composition or sprayable formulation, the number of colony forming units (cfu) per milliliter (ml) of said bacterial strain of current application in the microbial populations or bacterial populations or solutions or cultures or agricultural compositions or sprayable formulations will be at least $1\times10^6$ cfu/ml or at least $1\times10^7$ cfu/ml or at least $1\times10^8$ cfu/ml or at least $1\times10^9$ cfu/ml or at least $2\times10^9$ cfu/ml or at least $3\times10^9$ cfu/ml or at least $4\times10^9$ cfu/ml or at least $5\times10^9$ cfu/ml or at least $6\times10^9$ cfu/ml or at least $7\times10^9$ cfu/ml or at least $8\times10^9$ cfu/ml or at least $9\times10^9$ cfu/ml or at least $1\times10^{10}$ cfu/ml or at least $2\times10^{10}$ cfu/ml or at least $3\times10^{10}$ cfu/ml or at least $4\times10^{10}$ cfu/ml or at least $5\times10^{10}$ cfu/ml or at least $6\times10^{10}$ cfu/ml or at least $7\times10^{10}$ cfu/ml or at least $8\times10^{10}$ cfu/ml or at least $9\times10^{10}$ cfu/ml or at least $1\times10^{11}$ cfu/ml or at least $2\text{x}10^{11}$ cfu/ml or at least $3\times10^{11}$ cfu/ml or at least $4\times10^{11}$ cfu/ml or at least $5\times10^{11}$ cfu/ml or at least $6\times10^{11}$ cfu/ml or at least $7\times10^{11}$ cfu/ml or at least $8\times10^{11}$ cfu/ml or at least $9\times10^{11}$ cfu/ml or at least $1\times10^{12}$ cfu/ml or at least $1\times10^{13}$ cfu/ml or at least $1\times10^{14}$ cfu/ml.

Additional to the above detailed description of the invention, the following experimental details further enable the skilled person to put all details of the invention into practice.

Plant inoculation and growth conditions

*Caulobacter* strains were routinely grown in R2A medium (Reasoner and Geldreich 1985 Appl Environ Microbiol 49:1-7) at 28° C. To make bacterial inoculum, 1 ml of overnight culture was sub-cultured in 15 ml fresh R2A medium for 3 hours. Cells were collected by centrifugation, washed once and resuspended in phosphate buffered saline (PBS) solution. The bacterial concentration was adjusted to OD600=0.1 and further diluted by 10 (for seedling inoculation) or 1000 (for seed inoculation) times. For Arabidopsis seed inoculation, seeds were surface sterilized with chlorine gas and sown on square petri plates (120 mm×120 mm) with half strength Murashige and Skoog (MS) medium and 0.8% agar, with 5 seeds per plate. Subsequently, 1 μl PBS solution or bacterial inoculum was applied onto each seed for mock-treatment or bacterial inoculation, respectively. Next, plates were kept at 4° C. in the dark for 2 days to synchronize seed germination, and then placed vertically in growth chamber. For Arabidopsis seedling inoculation, seeds were sown and allowed to germinate in the same conditions. 4-day old seedlings (otherwise specified) were transferred to fresh half strength MS agar plates and inoculated with 8 μl PBS solution or bacterial inoculum per seedling. After inoculation, plants were grown vertically. Arabidopsis plants were grown in a growth chamber at 21° C. with a 16-h light/8-h dark photoperiod.

Terminology as used in describing the aspects of the invention is described in the following sections. In all herein described aspects and embodiments, "enhance" or "increase" or "improvement" refers to an at least 5% increase or at least 6% increase or at least 7% increase or at least 8% increase or at least 9% increase or at least 10% increase or at least 15% increase or at least 20% increase or at least 25% increase or at least 30% increase or at least 50% increase or at least 75% increase or at least a 100% increase in the property being measured.

For the purpose of current application, the term "bacterium" or "bacteria" includes any prokaryotic organism that does not have a distinct nucleus. While being both part of the group of microorganisms, bacteria and fungi are clearly distinct. The term "fungi" or "fungus" includes a wide variety of nucleated spore-bearing organisms that are devoid of chlorophyll. Examples of fungi include yeasts, molds, mildews, rusts and mushrooms.

In order to reconstruct the evolutionary relationships and sequence identity of one bacterial isolate to another, phylogenetic approaches are used standardly exploiting the 16S rRNA sequence or a portion of the 16S rRNA sequence of the bacteria, although any other sequence or the entire genome of the microorganisms to be analyzed can also be used. In microbiology, "16S rRNA sequence" refers to the sequence derived by characterizing the nucleotides that comprise the 16S ribosomal RNA gene(s). The bacterial 16S rRNA is approximately 1500 nucleotides in length.

In this application "sequence similarity", "sequence identity" and "sequence homology" are interchangeably used. The term "sequence identity" as used herein refers to the extent that sequences are identical on a nucleotide-by-nucleotide basis over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. A gap, i.e., a position in an alignment where a residue is present in one sequence but not in the other is regarded as a position with non-identical residues. Determining the percentage of sequence identity can be done manually, or by making use of computer programs that are available in the art. Examples of useful algorithms are PILEUP (Higgins & Sharp, CABIOS 5:151 (1989), BLAST and BLAST 2.0 (Altschul et al. J. Mol. Biol. 215: 403 (1990). Software for performing BLAST analyses is publicly available through the National Center for Biotechnology Information (http://www.ncbi.nlm.nih.gov/).

The present invention is described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The terms or definitions provided herein are solely to aid in the understanding of the invention. Unless specifically defined herein, all terms used herein have the same meaning as they would to one skilled in the art of the present invention. Practitioners are particularly directed to Michael R. Green and Joseph Sambrook, Molecular Cloning: A Laboratory Manual, 4th ed., Cold Spring Harbor Laboratory Press, Plainsview, N.Y. (2012); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

It is to be understood that although particular embodiments, specific configurations as well as materials and/or molecules, have been discussed herein for cells and methods according to the present invention, various changes or modifications in form and detail may be made without departing from the scope and spirit of this invention. The Examples described below are provided to better illustrate particular embodiments, and they should not be considered limiting the application. The application is limited only by the claims.

EXAMPLES

Example 1. Bacterial strains can promote plant growth under cold stress

A bacterial collection representing maize root endosphere families was established. 24 bacteria were selected from said collection and tested for maize growth promotion during cold stress. The different bacterial isolates were grown in liquid medium and diluted to $OD_{600}$ 0.02 using PBS buffer. For all maize experiments, surface-sterilized maize seeds were used. In brief, seeds were washed with sterile water (5 min); 70% ethanol (2 min); and bleach solution (20 min; 29 ml sterile water, 15 ml NaCIO, 12/13% stock solution 1 ml Tween20). Finally, the seeds were washed 5 times for 15 minutes with sterile water and dried before storage. Surface-sterilized seeds were pre-germinated for 48 h in the dark at 24° C. on 1% agar plates. Seedlings were inoculated while shaking for 3 h in a bacterial solution. As negative control, 15 seedlings were incubated in PBS buffer for 3 h. Inoculated and PBS-treated seedlings were sown in sand/perlite (50/50 volume%) and grown in controlled growth conditions (16 h light, day temperature 17° C.; 8 h dark, night temperature 12° C.). For each repeat, 15 plants were grown in separate pots; all pots of one treatment were put together in one tray. The entire tray was watered every two days (500 ml), while nutrients were added once a week (150 ml Hoagland's solution for 15 plants: 0.945 g/l, $Ca(NO_3)_2.4H_2O$, 0.506 g/l $KNO_3$, 0.136 g/l $KH_2PO_4$, 0.493 g/l $MgSO_4.7H_2O$, 2.5 ml/l FeEDTA stock (5.56 g $FeSO_4.7H_2O$, 7.46 g/l EDTA.Na)). After 30 days of growth, plants were harvested and shoot and root fresh weight were measured of inoculated and non-inoculated plants, together with plant length and the length of the fourth leaf. From the 24 strains tested, three genera showed a significant increase in total fresh weight (Table 1).

*Bosea* sp. RHG5 (Bradyrhizobiaceae-Bosea) shows a significant effect in all three repeats, increasing the fresh weight with an average of 18%. Inoculation with *Caulobacter* sp. RHG1 (Caulobacteraceae-Caulobacter) leads to an average increase in fresh weight of 25%. *Pseudoduganella* sp. RHG12 (Oxalobacteraceae-*Pseudoduganella*) had a positive effect in all repeats, increasing the total fresh weight with an average of 33% compared to the non-inoculated control.

TABLE 1

Maize seedlings are inoculated 3 h with bacterial solution (OD 0.02) or PBS as negative control before sowing. After 30 days of growth at cold temperatures (LD, 17° C. day, 12° C. night), total fresh weight is analyzed.

| Genus | Strain | % increase of fresh weight inoculated vs non-inoculated |
|---|---|---|
| *Bosea* | RHG5_repeat 1 | +14% (*) |
| | RHG5_repeat 2 | +28% (*) |
| | RHG5_repeat 3 | +13% (*) |
| *Caulobacter* | RHG1_repeat 1 | +20% (**) |
| | RHG1_repeat 2 | +34% (***) |
| | RHG1_repeat 3 | +20% |
| *Pseudoduganella* | RHG12_repeat 1 | +32% (***) |
| | RHG12_repeat 2 | +22% (***) |
| | RHG12_repeat 3 | +45% (***) |

*, $p < 0.05$;
**, $p < 0.01$;
***, $p < 0.001$

Example 2. *Caulobacter* RHG1 promotes plant growth in dicots as well

Figure 1B:
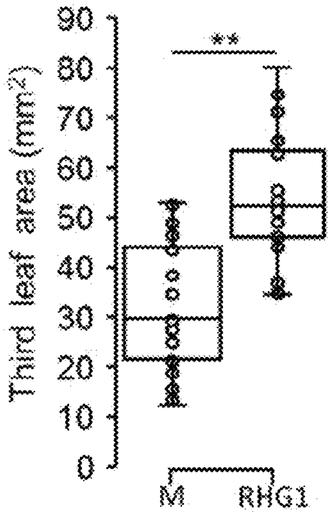
Figure 1C:
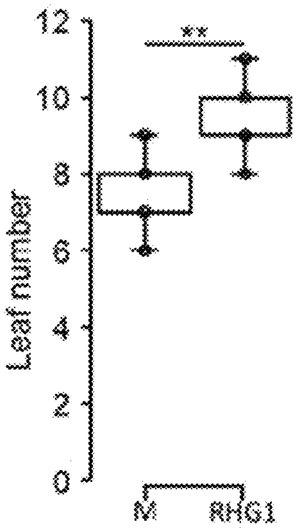
Figure 1D:
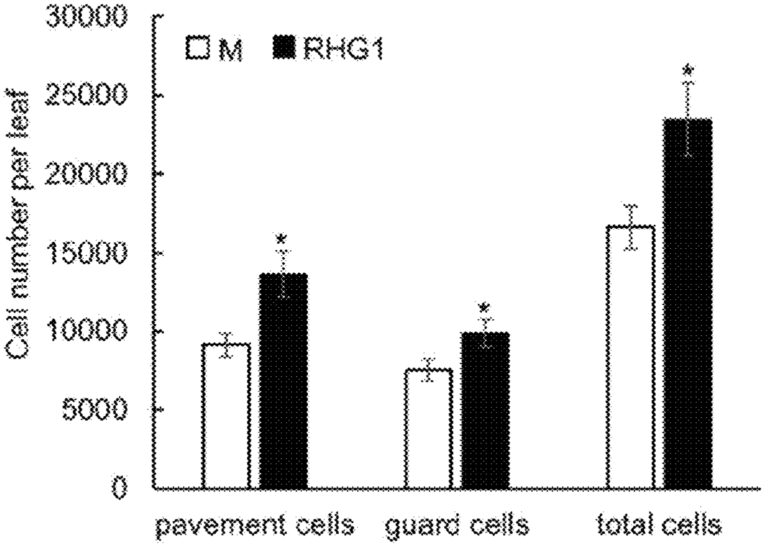
Figure 2A:
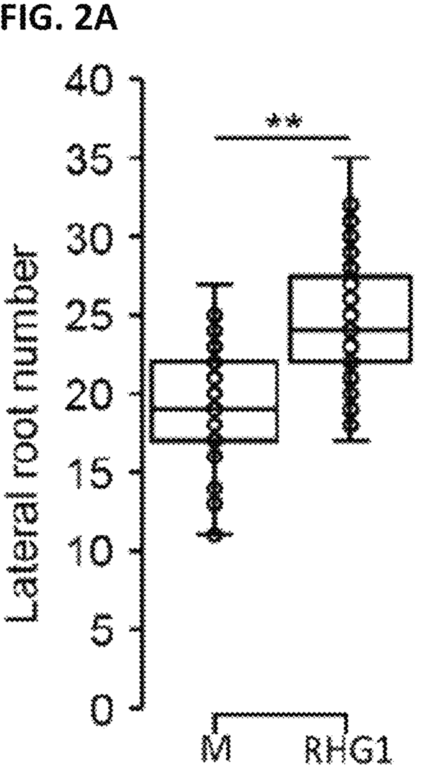
FIGS. 2A-2B illustrates the root growth promoting effect of *Caulobacter* strain RHG1. M, mock. The plot graphs are based on three biological replicates (n≥12 for each treatment). Asterisks indicate statistical significance between mock and inoculated plants (**, p<0.01, Student's t-test).
Figure 2B:
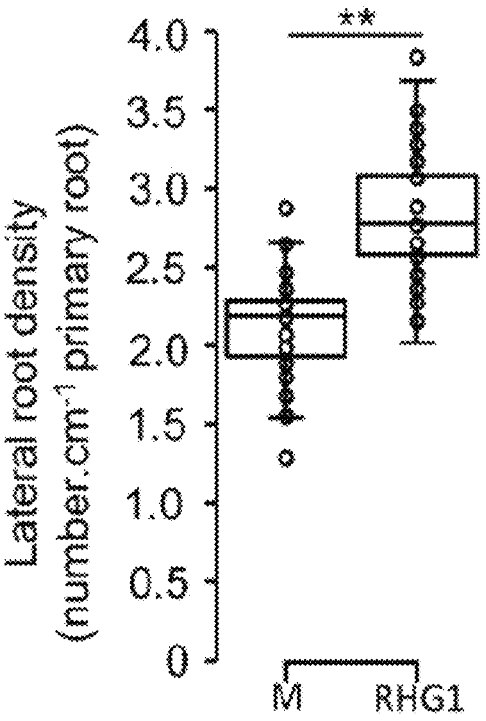

To test whether the cold-tolerance-inducing bacteria disclosed in Example 1 also affects plant growth in optimal temperature conditions, the PGP effect of the *Caulobacter* strain RHG1 was studied using the dicot Arabidopsis. Arabidopsis seeds were inoculated with RHG1, as described in the detailed description. At 18 days after germination (DAG), fresh weight of both shoot and root was significantly increased by bacterial inoculation (FIG. 1A). In the shoot, increase in both leaf area (size) and total leaf number contributed to the increase of shoot biomass of the inoculated plants (FIG. 1B-C). Furthermore, cellular analysis of leaf epidermis revealed that RHG1-inoculated plants had increased number of pavement cells, guard cells, and accordingly total epidermal cells compared to the mock treated plants (FIG. 1D). Interestingly, the pavement cells in the leaves of RHG1-inoculated plants were significantly smaller than mock treated plants (data not shown), suggesting that increase of leaf size by RHG1 is a result of increase of cell number instead of cell area. In order to assess the influence of *Caulobacter* sp. RHG1 on the growth of the root system, the lateral root number and lateral root density were determined at 14 DAG. RHG1 inoculation had a consistent and positive effect on lateral root number and lateral root density in all of the experiments performed (FIG. 2A-B), which contributed to the increase of root biomass of the inoculated plants.

Figure 3:
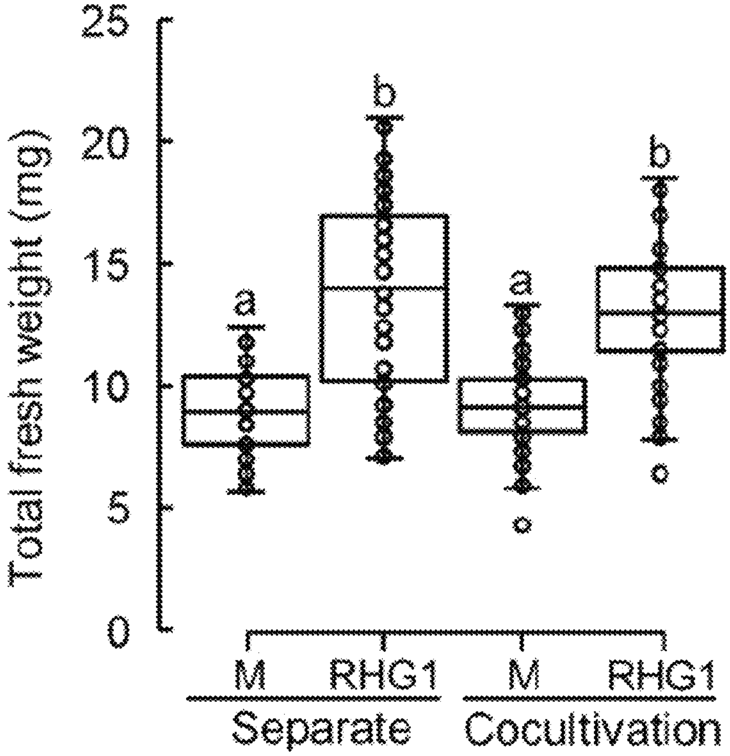
FIG. 3 shows the fresh weight of mock-treated (M) or RHG1-inoculated (RHG1) Arabidopsis plants grown in the separate or cocultivation setup determined at 14 DAIG. The boxplot presents the combined data from three independent experiments with at least 20 plants per treatment in each experiment. Different letters indicate significantly different statistical groups (p<0.01, Tukey's Honest Significance Difference test).

In order to assess if the PGP effect of RHG1 was caused by bacterial production of $CO_2$ or other easily diffusible volatile compounds, we used a co-cultivated set-up and tested if mock-treated plants grown next to RHG1-inoculated plants in the same plate could benefit from the bacteria. We found that in the co-cultivated set-up the fresh weight of RHG1-inoculated plants was significantly higher than the mock-treated plants, and the increase of fresh weight by RHG1 in the co-cultivated set-up was not significantly different from the separated set-up in which the RHG1-inoculated and mock-treated plants were grown in different plates (FIG. 3). This result showed that the PGP effect of RHG1 is not caused by $CO_2$ or other easily diffusible volatile compounds.

Figure 9:
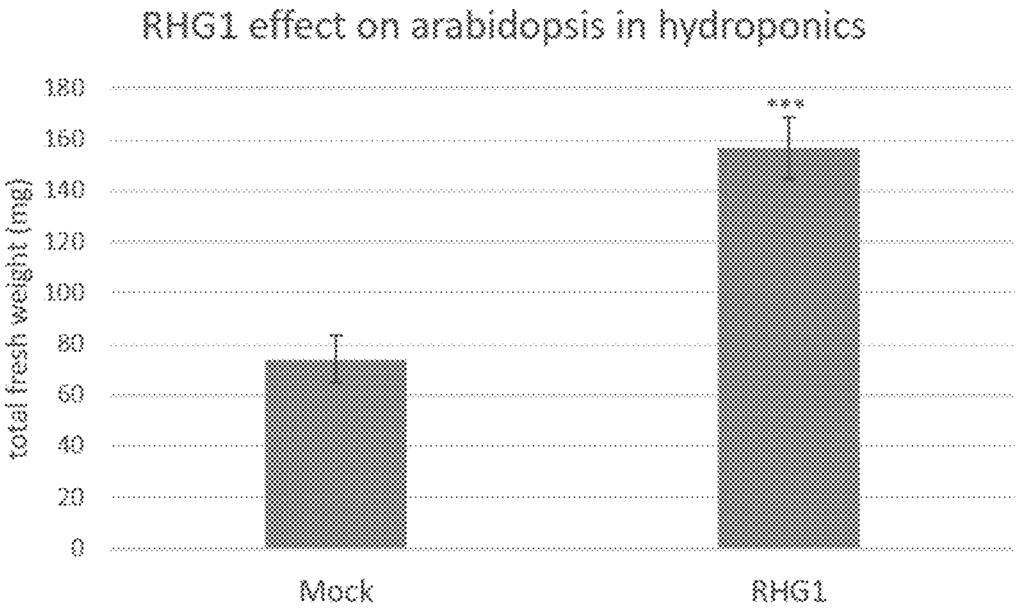
FIG. 9 shows the effect of *Caulobacter* sp. RHG1 on Arabidopsis (total fresh weight in mg) grown in a hydroponics system.
Figure 10:
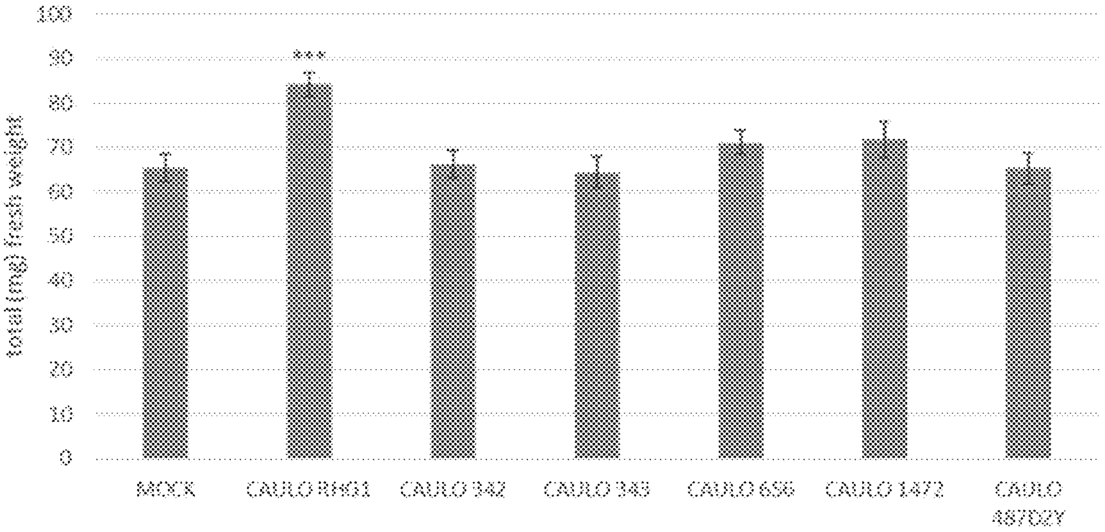
FIG. 10 shows the results of a comparative analysis between the growth promoting effect of the *Caulobacter* strain of the application (RHG1) and 5 additional *Caulobacter* strains (i.e. strains 342, 343, 656, 1472 and 487D2Y).

Next, the effect of *Caulobacter* RHG1 was checked on Arabidopsis grown in a hydroponics system. Arabidopsis seedlings were first inoculated (500 µl $OD_{600}$ 0.01) at 2 days old and a second time at 9 days after germination (500 µl $OD_{600}$ 0.01). The plants were harvested 4 weeks after sowing and shoot and root fresh weight was measured. In line with the above the *Caulobacter* RHG1 treated plants promoted the growth significantly (FIG. 9). Finally, we compared the plant-growth promoting effect of Caulobacter RHG1 with that of five other *Caulobacter* strains described in Bai et al (2015 Nature 528:364-372). Based on a 16S rRNA blast analysis, strains 342 and 343 show the highest homology to C. segnis, while strains 656 and 1472 show the highest homology to C. rhizosphaerae and C. henricii. Of each strain a bacterial suspension was made by growing the bacterial strains in R2A medium overnight, followed by a subculturing for 6h, washing and diluting with PBS to $OD_{600}$ 0.01. Arabidopsis seedlings were inoculated at 4 days after germination. Root and shoot fresh weight were measured 14 days after inoculation. Surprisingly, none of the other five strains could statistically significantly affect the total fresh weight of treated plants (FIG. 10). In contrast, treatment of plants with the herein described *Caulobacter* strain RHG1 increased the plants' total fresh weight with almost 30% (FIG. 10). These data clearly demonstrate that the described plant promoting effect is not a general characteristic within the *Caulobacter* genus and neither among the C. segnis species.

Figure 4A:
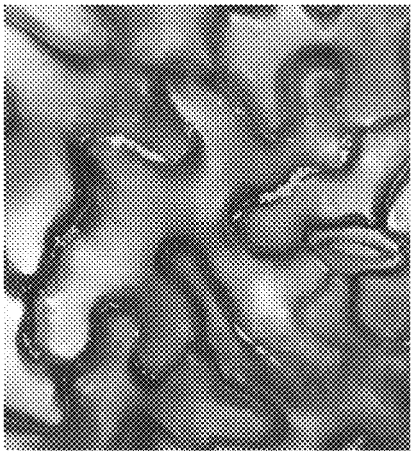
FIGS. 4A-4C is a selection of representative confocal microscopic images of Arabidopsis tissues colonized by strain RHG1::GFP.
Figure 4B:
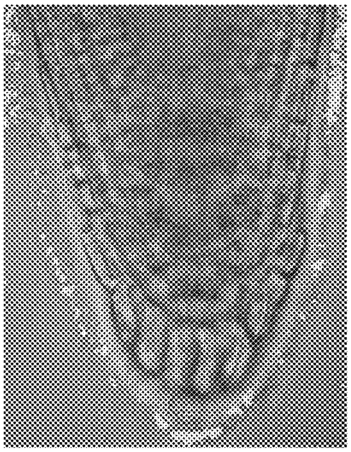
Figure 4C:
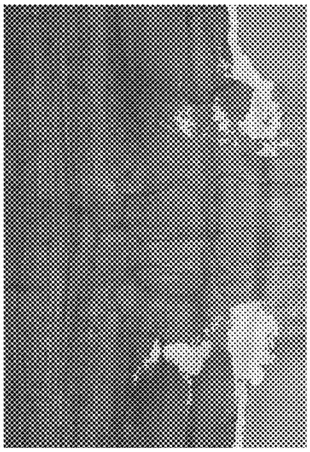

Example 3. *Caulobacter* RHG1 colonizes the plant root system Next, it was investigated whether RHG1 could enter the plant and live as an endophyte. The colonization of RHG1 on Arabidopsis shoot and root was determined by colony forming units per milligram of fresh weight (CFU/mg FW). At 14 DAG, the overall CFU was in the range of $10^6$-$10^7$ (average $8.81\times10^6$) or $10^6$-$10^8$ (average $9.51\times10^7$) CFU/mg fresh weight in the shoot or root, respectively. In order to investigate the colonization pattern of RHG1 via microscopic analysis, we labeled RHG1 with GFP by using mini-Tn5 based transposon delivery system (Tombolini et al., 1997), which allowed the insertion of the GFP marker driven by a constitutive PpsbA promoter into the chromosome of the bacteria. The resulting strain is referred to as RHG1::GFP hereafter. Plants inoculation with the RHG1::GFP strain had increased shoot and root weight compared to the mock-treated control (data not shown). There was no significant difference in terms of fresh weight between the RHG1::GFP-inoculated and the RHG1-inoculated plants, indicating that the insertion of the GFP marker into the genome does not disturb the interaction of the bacteria with plants. We then analyzed the colonization pattern of RHG1::GFP using confocal microscopy. At 14 DAG, colonization of RHG1::GFP was observed on the leaf surface and root surface (FIG. 4A-B). Additionally, at sites where lateral roots emerged, GFP signal was observed in between the plant cells (FIG. 4C). The data could be confirmed using fixed and cleared plant tissue (data not shown). Hence, RHG1 colonizes the root and leaf surfaces and enters the root at lateral root basis although in a superficial way.

Figure 5:
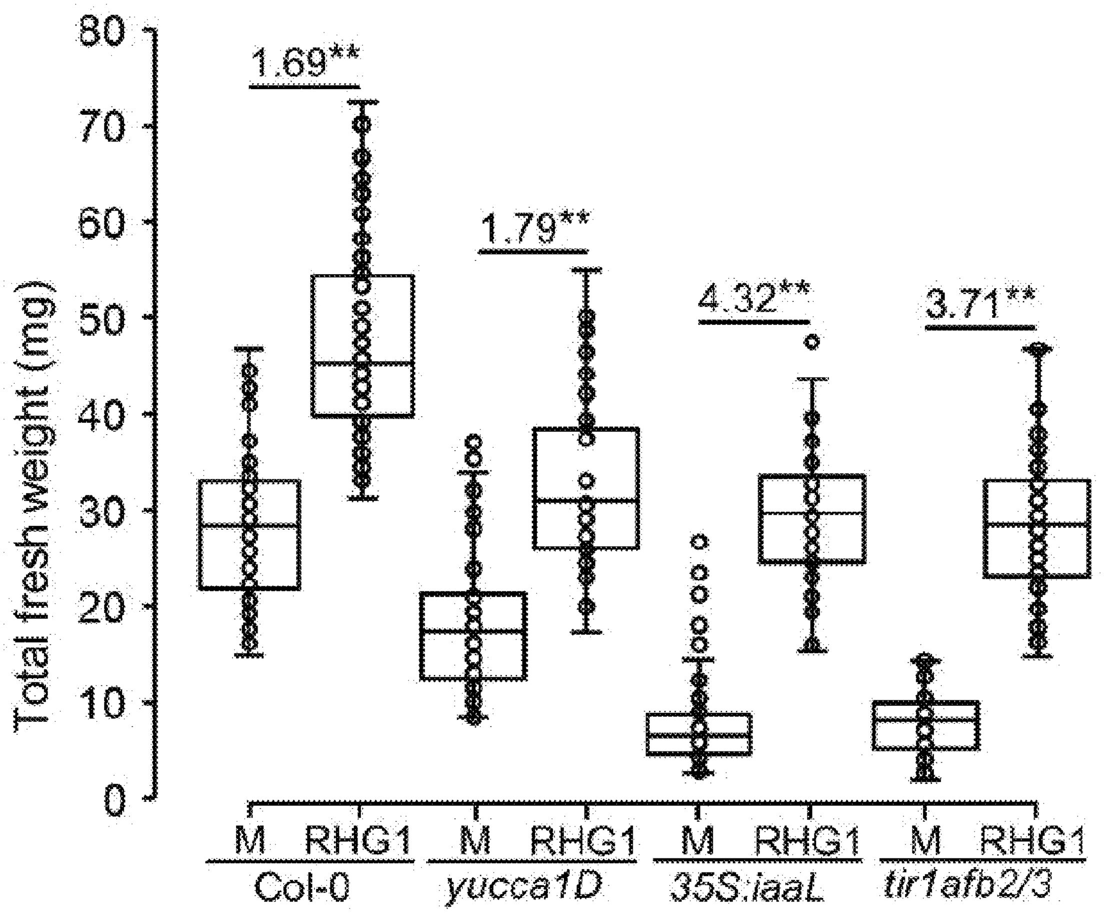
FIG. 5 shows the effect of RHG1 on total plant fresh weight of the Col-0, yucca1D, 35S:iaaL and tir1afb2/3 Arabidopsis genotypes. Seeds were mock-treated (M) or inoculated with RHG1 (RHG1). Fresh weight was determined at 18 DAIG from at least 15 plants per treatment. Results of three independent replicates were combined and shown in the plot graph. The value on top of the two boxes of each genotype indicates the fold-change in weight between mock-treated (M) and RHG1-inoculated (RHG1) plants. Asterisks indicate statistical significance between mock and RHG1-inoculated plants (**, p<0.01, Student's t-test).
Figure 6A:
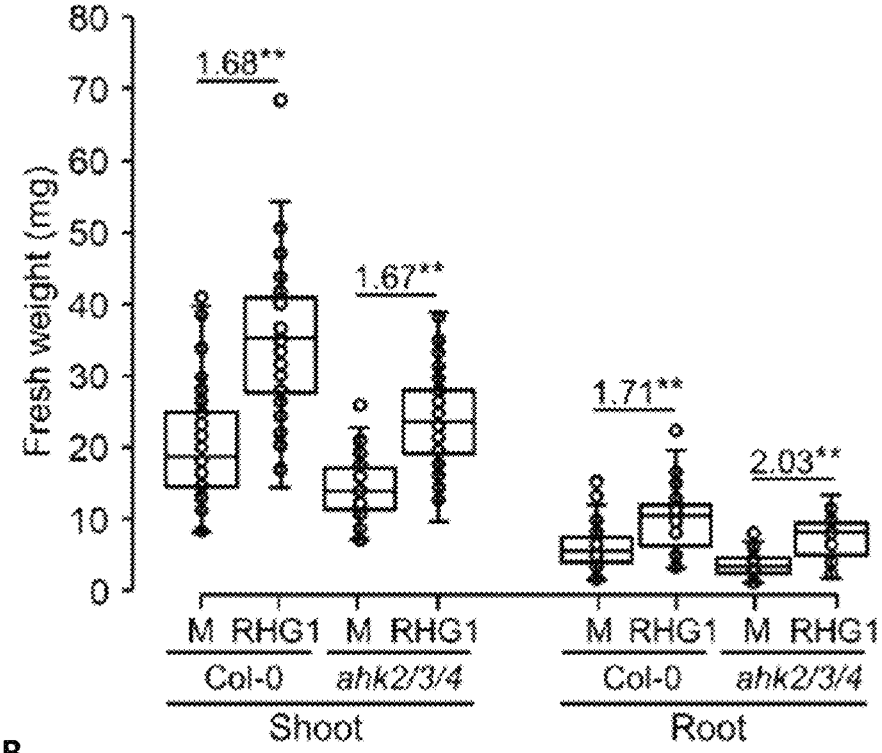
FIGS. 6A-6B shows the effect of RHG1 on shoot and root fresh weights of Arabidopsis genotypes affected in cytokinin (i.e. ahk2/3/4, see FIG. 6A) or ethylene signalling (i.e. ein2-5, see FIG. 6B) pathways compared to control plants (Col-0). Seeds were mock-treated (M) or inoculated with RHG1 (RHG1). Fresh weight was determined at 18 DAIG from at least 20 plants per treatment. Results of four independent replicates were combined and shown in the plot graphs. The value on top of the two boxes of each genotype indicates the fold change in weight between mock-treated (M) and RHG1-inoculated (RHG1) plants. Asterisks indicate statistical significance between mock and inoculated plants (**, p<0.01, Student's t-test).
Figure 6B:
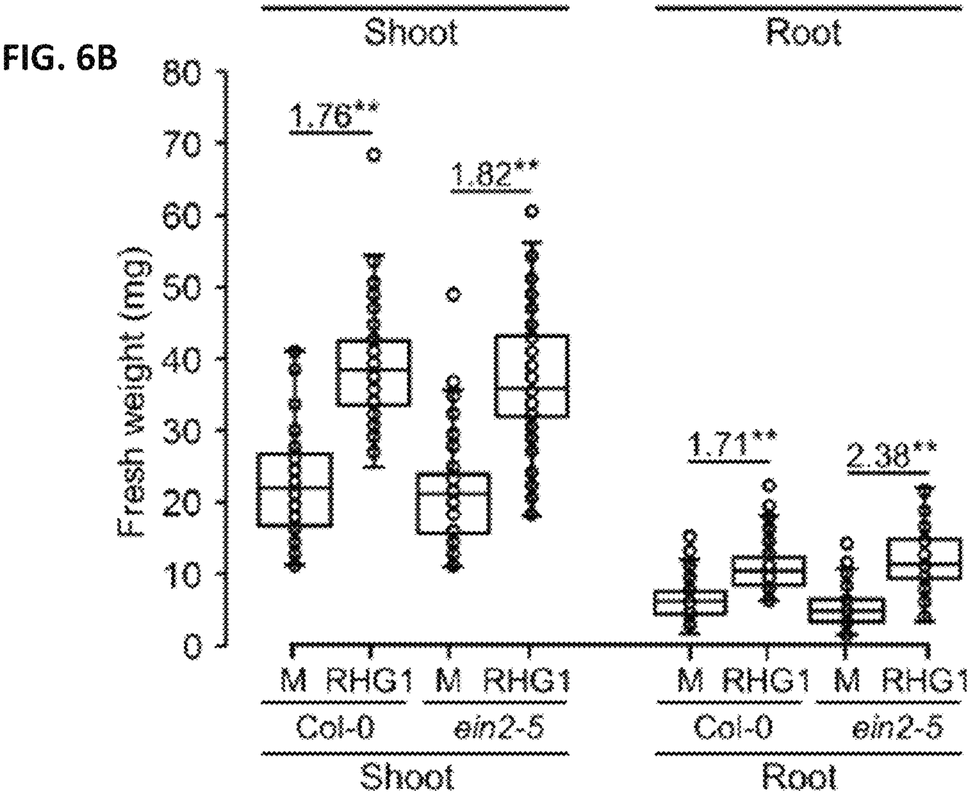

Example 4. *Caulobacter* RHG1 promotes plant growth in an auxin-, cytokinin- and ethylene-independent manner Bacterial production of auxins, cytokinins or ethylene is frequently found to be a PGP trait in many PGP rhizobacteria. Surprisingly, pathways or genes responsible for production of these plant hormones were not found in the genome of RHG1. To check whether *Caulobacter* sp. RHG1 indeed promotes plant growth in an auxin-independent manner, a selection of plants affected in auxin signalling were tested for the RHG1-mediated PGP effect, i.e. yuccalD, 35S::iaaL and tir1afb2afb3. yuccalD is an IAA overproducing gain-of-function mutant (Zhao et al., 2001). Indole-3-acetic acid (IAA or 3-IAA) is the most common, naturally occurring, plant hormone of the auxin class. It is the best known of the auxins and has been the subject of extensive studies by plant physiologists. The 35S:iaaL line overexpresses the bacterial IAA lysine synthase that inactivates IAA (Jensen et al., 1998), while tir1afb2afb3 is an auxin signalling mutant deficient in the auxin receptors TIR1, AFB2 and AFB3 (Dharmasiri et al., 2005). Our result showed that the increase of plant fresh weight by RHG1 was not attenuated in any of those auxin mutant or transgenic lines compared to the wild type Col-0 (FIG. 5). Hence, the plant growth promoting effect of *Caulobacter* strain RHG1 is independent from the plant hormone auxin. Also the possible involvement of the plant hormones cytokinin and ethylene was tested. The ahk2ahk3ahk4 triple mutant, which is impaired in cytokinin signaling due to mutations in the cytokinin receptor AHK2, AHK3 and AHK4 (Nishimura et al., 2004), still had significant growth promotion by RHG1 in terms of fresh root and shoot weight (FIG. 6A). Similarly, the RHG1-mediated increase of plant weight was not attenuated the ethylene insensitive mutant ein2-5, which is deficient in ethylene signal transduction due to a null mutation in the ETHYLENE INSENSITIVE2 (EIN2) gene (Wang et al., 2007), compared to the wild type Col-0 (FIG. 6B).

Collectively, our data show that the attenuated PGP effect of the *Caulobacter* strain RHG1 does not depend on the above mentioned hormones.

Example 5. *Caulobacter* RHG1 promotes lettuce growth

Figure 7A:
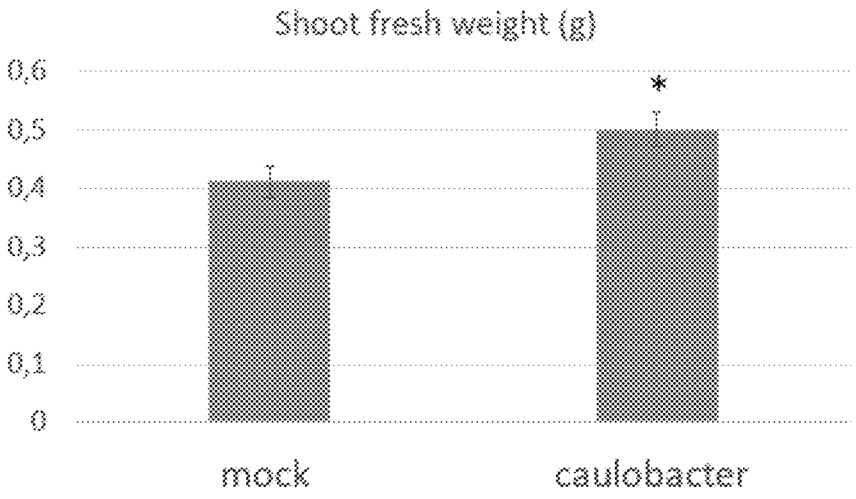
FIGS. 7A-7C shows the plant growth promoting effect of the RHG1 *Caulobacter* strain on lettuce plants.
Figure 7B:
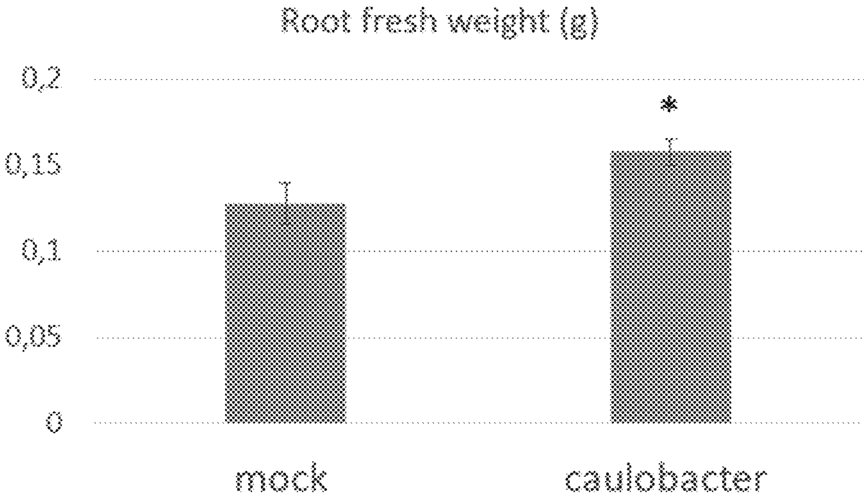
Figure 7C:
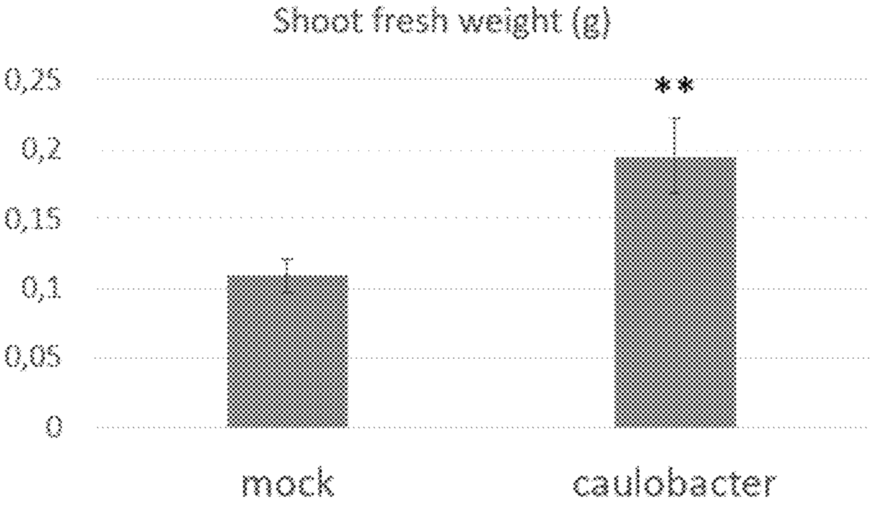

Lettuce seeds (cultivar Presteria) were sown in an in-house hydroponic set-up. In brief, lettuce seeds were sown in sand filled cups which are constantly in touch with a Hoagland nutrient solution. The solution reaches the seeds sown on top of the sand filled cups through capillary forces. The experiment is performed in a WEIS growth chamber set at 8/12 degrees Celsius (day/night) with long day conditions (16h light, 8h dark). Two days after germination the seedlings are inoculated with 1 ml *Caulobacter* RHG1 at OD 0.01 in PBS. A second identical inoculation occurred (inoculation =pipetting 1 ml of bacterial solution directly onto the seedling) 7 days later. At 30 days after sowing, the plants were harvested (above ground parts and the roots) to determine their fresh weight. Interestingly but in line with the above described plant growth promoting activity of RHG1, both the shoot fresh weight as the root fresh weight was significantly increased upon RHG1 treatment compared to untreated lettuce seeds (FIG. 7A-7B). Next, inoculated versus non-inoculated lettuce seedlings were also grown in peat blocks. The same settings were used: WEIS growth chamber set at 8/12° C. (day/night) with long day conditions (16 h light, 8 h dark). Seedlings were inoculated with RHG1 for two hours on a shaker in a RHG1 solution of OD 0.01 in PBS. Six weeks after sowing, the above ground parts plants were harvested. The RHG1-inoculated plants showed an almost double shoot fresh weight compared to the non-inoculation lettuce plants (FIG. 7C).

Example 6. *Caulobacter* RHG1 promotes salt tolerance in tomato The plant growth promoting effect of RHG1 was also tested in salt stress condition using tomato seedlings. Solanum lycopersicum cv. Micro-Tom seeds were sterilized by rinsing them in 70% EtOH for 3 min, washed a couple of times with sterile water and then transferred to 4% of bleach for 5 minutes.

Figure 8A:
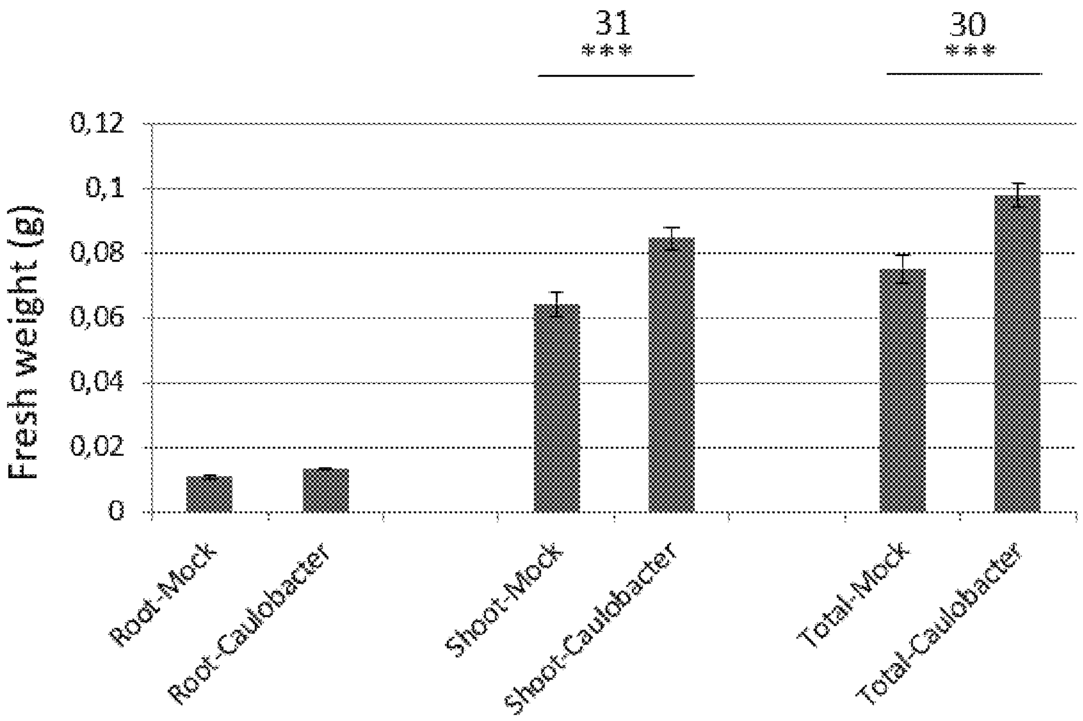
FIGS. 8A-8B shows the plant growth promoting effect of the *Caulobacter* RHG1 strain on tomato plants grown under salt stress.
Figure 8B:
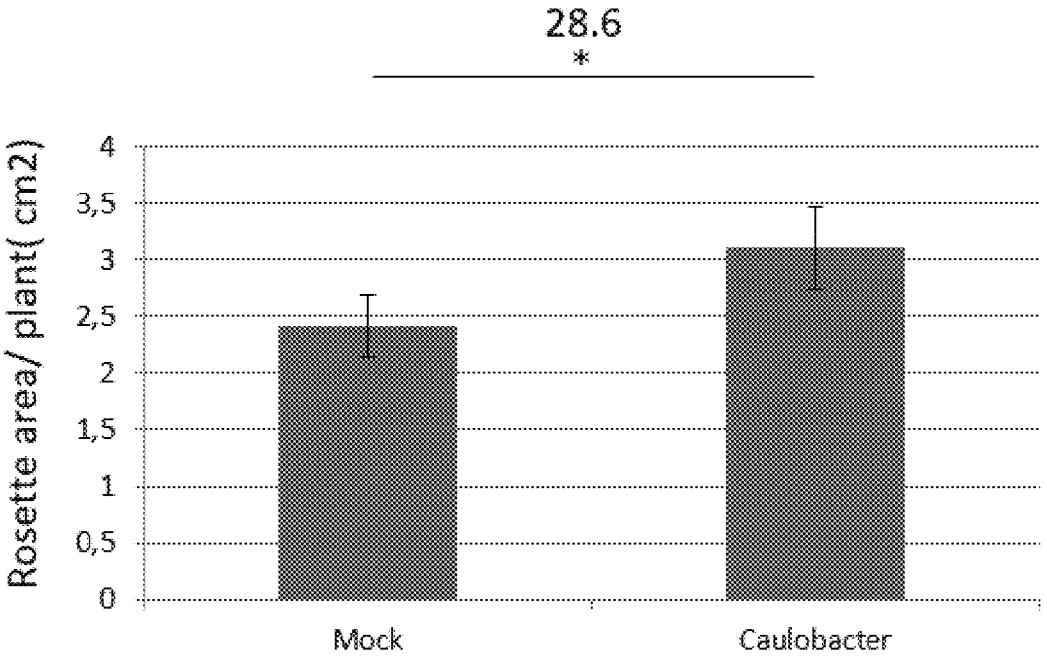

Next, the seeds were washed five times with sterilized $H_2O$, after which they were dried in a flow chamber. The sterilized tomato seeds were first sown on agar plates (0.5×MS), put at 4° C. for 2 days and subsequently at 24° C. for 1 day in dark to synchronize germination. Three days later, uniform germinated tomatoes were transferred to new plates (0.5×MS) with (150 mM) or without (0 mM) NaCl and treated with RHG1 suspension in PBS ($0D_{540}$=0.001) or PBS only (mock). The root fresh weight, shoot fresh weight, total fresh weight were measured at 18 days after transfer with three repeats in total. As expected, salt treatment dramatically reduced root and shoot growth (FIG. 8A). However the decrease in shoot fresh weight observed in RHG1-treated seedlings was significantly less pronounced than that of mock-treated seedlings. Also the rosette area of the plants inoculated with RHG1 and grown in the presence of 150 mM NaCl was significantly higher than that of mock treated seedlings grown on NaCl (FIG. 8B).

To summarize: all the above results clearly show that the *Caulobacter* strain RHG1 is a plant growth promoting bacterium improving plant growth in optimal conditions (Example 2 and 5) but also during cold stress (Example 1) and salt stress (Example 6).

The invention claimed is:

1. A composition comprising a bacterial strain comprising a 16S rRNA sequence, having at least 99.6% sequence identity to SEQ ID No. 1; and wherein the composition further comprises an effective amount of a preservative.

2. A plant seed coated with an isolated bacterial strain comprising a 16S rRNA sequence having at least 99.6% sequence identity to SEQ ID No. 1.

3. A method for enhancing growth, yield, cold tolerance and/or salt tolerance of a plant, the method comprising:

inoculating a plant growth medium with a microbial population, said population at least one plant growth-promoting comprising a bacterial strain comprising a 16S rRNA sequence having at least 99.6% sequence identity to SEQ ID No. 1; and growing a plant in said plant growth medium;

to enhance growth, yield, cold tolerance and/or salt tolerance of said plant.

4. The method of claim 3, wherein the microbial population is applied to the plant growth medium as a powder, as a pellet, as a granule, as a liquid.

5. A method for enhancing growth, yield, cold tolerance and/or salt tolerance of a plant, the method comprising:

growing a plant in an environment that supports plant growth; and administering a sprayable formulation to the environment or to the plant, the formulation comprising a bacterial strain comprising a 16S rRNA sequence having at least 99.6% sequence identity to SEQ ID No. 1;

to obtain enhanced growth, yield, cold tolerance and/or salt tolerance of said plant.

6. The composition of claim 1, wherein the bacterial strain is the *Caulobacter* sp. strain RHG1 with deposit number LMG P-31259.

7. The plant seed of claim 2, wherein the isolated bacterial strain is the *Caulobacter* sp. strain RHG1 with deposit number LMG P-31259.

8. The method according to claim 5 wherein the bacterial strain is the *Caulobacter* sp. strain RHG1 with deposit number LMG P-31259.

9. The method according to claim 5 wherein the bacterial strain is the *Caulobacter* sp. strain RHG1 with deposit number LMG P-31259.

* * * * *

SEQUENCE LISTING

<160> NUMBER OF SEQ ID NOS: 3

<210> SEQ ID NO 1
<211> LENGTH: 1441
<212> TYPE: DNA
<213> ORGANISM: Caulobacter sp. RHG1

<400> SEQUENCE: 1

```
agcgaacgct ggcggcaggc ctaacacatg caagtcgaac ggatccttcg ggattagtgg     60

cggacgggtg agtaacacgt gggaacgtgc cttttggttc ggaacaactc agggaaactt    120

gagctaatac cggatgtgcc cttcgggga aagatttatc gccattagag cggcccgcgt    180

ctgattagct agttggtggg gtaaaggccc accaaggcga cgatcagtag ctggtctgag    240

aggatgatca gccacattgg gactgagaca cggcccaaac tcctacggga ggcagcagtg    300

gggaatcttg cgcaatgggc gaaagcctga cgcagccatg ccgcgtgaat gatgaaggtc    360

ttaggattgt aaaattcttt caccggggac gataatgacg gtacccggag aagaagcccc    420

ggctaacttc gtgccagcag ccgcggtaat acgaaggggg ctagcgttgc tcggaattac    480

tgggcgtaaa gggagcgtag gcggactgtt aagttagagg tgaaagccca gggctcaacc    540

ttggaattgc ctttgatact ggcagtcttg agtacggaag aggtatgtgg aactccgagt    600

gtagaggtga aattcgtaga tattcggaag aacaccagtg gcgaaggcga catactggtc    660

cgttactgac gctgaggctc gaaagcgtgg ggagcaaaca ggattagata ccctggtagt    720

ccacgccgta aacgatgagt gctagttgtc ggcatgcatg catgtcggtg acgcagctaa    780

cgcattaagc actccgcctg gggagtacgg tcgcaagatt aaaactcaaa ggaattgacg    840

ggggcccgca caagcggtgg agcatgtggt ttaattcgaa gcaacgcgca gaaccttacc    900

acctttgac atgcctggac atccagagag atctggcttt cccttcgggg actgggacac    960

aggtgctgca tggctgtcgt cagctcgtgt cgtgagatgt tgggttaagt cccgcaacga   1020

gcgcaaccct cgcgattagt tgccatcagg tttggctggg cactctaatc gtactgccgg   1080

agttaatccg gaggaaggcg gggatgacgt caagtcctca tggcccttac aaggtgggct   1140

acacacgtgc tacaatggcg actacagagg gctgcaatcc cgcgaggggg agccaatccc   1200

taaaagtcgt ctcagttcgg attgttctct gcaactcgag agcatgaagt tggaatcgct   1260

agtaatcgcg gatcagcatg ccgcggtgaa tacgttcccg ggccttgtac acaccgcccg   1320

tcacaccatg ggagttggct ttacccgaag gcgctgcgct aactcgcaag agaggcaggc   1380

gaccacggta gggtcagcga ctggggtgaa gtcgtaacaa ggtagccgta ggggaacctg   1440

c                                                                   1441
```

<210> SEQ ID NO 2
<211> LENGTH: 1002
<212> TYPE: DNA
<213> ORGANISM: Bosea sp. RHG5

<400> SEQUENCE: 2

```
tgcaagtcga acgggcactt cggtgctagt ggcagacggg tgagtaacac gtgggaacgt     60

acctttcggt tcggaataat acagggaaac ttgtactaat accggatacg cccttcgggg    120

gaaagattta tcgccgatag atcggcccgc gtctgattag ctagttggtg aggtaatggc    180

tcaccaaggc gacgatcagt agctggtctg agaggatgat cagccacact gggactgaga    240

cacggcccag actcctacgg gaggcagcag tggggaatat tggacaatgg gcgaaagcct    300

gatccagcca tgccgcgtgt gtgatgaagg ccttagggtt gtaaagcact tttgtccggg    360
```

-continued

```
aagataatga ctgtaccgga agaataagcc ccggctaact tcgtgccagc agccgcggta    420

atacgaaggg ggctagcgtt gctcggaatc actgggcgta aagggcgcgt aggcggactt    480

ttaagtcggg ggtgaaagcc cagggctcaa ccctggaatt gccttcgata ctgagagtct    540

tgagttcgga agaggttggt ggaactgcga gtgtagaggt gaaattcgta gatattcgca    600

agaacaccag tggcgaaggc ggccaactgg tccgatactg acgctgaggc gcgaaagcgt    660

ggggagcaaa caggattaga taccctggta gtccacgccg taaacgatga atgccagccg    720

ttggggtgca tgcacctcag tggcgcagct aacgctttaa gcattccgcc tggggagtac    780

ggtcgcaaga ttaaaaactc aaaggaattg acgggggccc gcacaagcgg tggagcatgt    840

ggcttaattc gaagcaacgc gcagaacctt accagctttt tgacattgtc cggtttgatc    900

ggcagagatg cctttttcttc agttcggctg gccggaacac atgtgctgca tgggctgtcg    960

tcagctcgtg tcgtgagatg ttgggttaag tccgcaacga gc                      1002
```

<210> SEQ ID NO 3
<211> LENGTH: 1397
<212> TYPE: DNA
<213> ORGANISM: Pseudoduganella sp. RHG12

<400> SEQUENCE: 3

```
tgcagtcgaa cggcagcgcg ggggcaaccc tgggcggcga gtggcgaacg ggtgagtaat     60

atatcggaac gtacccaaga gtgggggata acgtagcgaa agttacgcta ataccgcata    120

cgatctaagg atgaaagcag gggatcgcaa gaccttgtgc tcctggagcg gccgatatct    180

gattagctag ttggtggggt aaaggcccac caaggcaacg atcagtagct ggtctgagag    240

gacgaccagc cacactggaa ctgagacacg gtccagactc ctacgggagg cagcagtggg    300

gaattttgga caatgggggc aaccctgatc cagcaatgcc gcgtgagtga agaaggcctt    360

cgggttgtaa agctcttttg tcagggaaga aaagggtctg gctaatatcc agatctgctg    420

acggtacctg aagaataagc accggctaac tacgtgccag cagccgcggt aatacgtagg    480

gtgcaagcgt taatcggaat tactgggcgt aaagcgtgcg caggcggttt cgtaagtctg    540

tcgtgaaatc cccgggctta acctgggaat ggcgatggag actgcgaggc tagagtttgg    600

cagagggggg tagaattcca cgtgtagcag tgaaatgcgt agagatgtgg aggaacaccg    660

atggcgaagg cagccccctg ggtcaaaact gacgctcatg cacgaaagcg tggggagcaa    720

acaggattag ataccctggt agtccacgcc ctaaacgatg tctactagtt gttgggtctt    780

aattgactta gtaacgcagc taacgcgtga agtagaccgc ctggggagta cggtcgcaag    840

attaaaactc aaaggaattg acggggaccc gcacaagcgg tggatgatgt ggattaattc    900

gatgcaacgc gaaaaacctt acctaccctt gacatggcag gaatcccgga gagatttggg    960

agtgctcgaa agagaacctg cacacaggtg ctgcatggct gtcgtcagct cgtgtcgtga   1020

gatgttgggt taagtcccgc aacgagcgca acccttgtca ttagttgcta cgcaagagca   1080

ctctaatgag actgccggtg acaaaccgga ggaaggtggg gatgacgtca agtcctcatg   1140

gcccttatgg gtagggcttc acacgtcata caatggtaca tacagagggc cgccaacccg   1200

cgagggggag ctaatcccag aaagtgtatc gtagtccgga ttgtagtctg caactcgact   1260

acatgaagtt ggaatcgcta gtaatcgcgg atcagcatgt cgcggtgaat acgttcccgg   1320

gtcttgtaca caccgcccgt cacaccatgg gagcgggttt taccagaagt aggtagctta   1380

accgcaagga gggcgct                                                  1397
```